United States Patent
Wood et al.

(10) Patent No.: US 6,846,929 B2
(45) Date of Patent: Jan. 25, 2005

(54) BENZOTRIAZOLE/HALS MOLECULAR COMBINATIONS AND COMPOSITIONS STABILIZED THEREWITH

(75) Inventors: Mervin G. Wood, Poughquag, NY (US); Jacqueline Lau, Jericho, NY (US); Ramanathan Ravichandran, Suffern, NY (US); Andrea R. Smith, Wingdale, NY (US); Joseph Suhadolnik, Yorktown Heights, NY (US); Peter Solera, Suffern, NY (US); Joseph S. Puglisi, Ossining, NY (US); Carmen Hendricks-Guy, White Plains, NY (US); Stephen D. Pastor, Danbury, CT (US); Luther A. R. Hall, Woodcliff Lake, NJ (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 327 days.

(21) Appl. No.: 09/824,147

(22) Filed: Apr. 2, 2001

(65) Prior Publication Data

US 2003/0074833 A1 Apr. 24, 2003

(51) Int. Cl.$^7$ ............................................. C07D 401/12
(52) U.S. Cl. ..................................................... 546/199
(58) Field of Search ........................................ 546/199

(56) References Cited

U.S. PATENT DOCUMENTS

| | | | |
|---|---|---|---|
| 3,530,084 A | 9/1970 | Potts ........................ | 260/28.5 |
| 4,278,590 A | 7/1981 | Dexter et al. ............... | 260/45.8 |
| 4,289,686 A | 9/1981 | Rody et al. ................. | 260/45.8 |
| 4,314,933 A | 2/1982 | Berner ..................... | 260/45.75 |
| 4,379,721 A | 4/1983 | Qualitz et al. ............... | 106/21 |
| 4,481,315 A | 11/1984 | Rody et al. .................... | 524/89 |
| 5,021,478 A | 6/1991 | Ravichandran et al. ........ | 524/91 |
| 5,278,310 A | 1/1994 | Raspanti ..................... | 546/222 |
| 5,280,124 A | 1/1994 | Winter et al. ................ | 548/259 |
| 5,382,588 A | 1/1995 | Raspanti ..................... | 514/315 |
| 5,616,051 A | 4/1997 | Rogers et al. ................ | 439/518 |
| 5,879,694 A | 3/1999 | Morrison et al. ............. | 424/405 |
| 5,964,905 A | 10/1999 | Camp et al. ................... | 44/275 |
| 6,166,218 A | 12/2000 | Ravichandran et al. ..... | 548/257 |
| 6,407,254 B1 | 6/2002 | Riva et al. ................... | 548/260 |

FOREIGN PATENT DOCUMENTS

| | | |
|---|---|---|
| EP | 0005922 | 12/1979 |
| EP | 0359488 | 3/1990 |
| EP | 0133964 | 7/1990 |
| EP | 0704560 | 1/1999 |
| JP | 3278554 | 12/1991 |
| WO | 94/13736 | 6/1994 |
| WO | 99/23093 | 5/1999 |
| WO | 00/22037 | 4/2000 |
| WO | 01/56998 | 8/2001 |
| WO | 01/57125 | 8/2001 |

OTHER PUBLICATIONS

Ullmann's Encyclopedia of Industrial Chemistry, vol. A5, pp. 29–30.
F. A. Ballentine et al., National Candle Association Technical Meeting on Apr. 16, 1998, "Inhibiting Color Fading of Dyed Candles with CYASORB®".
Abstract for JP 3278554 (1991).

*Primary Examiner*—Laura L. Stockton
(74) *Attorney, Agent, or Firm*—Tyler A. Stevenson

(57) ABSTRACT

Compounds which have a benzotriazole and a hindered amine moiety in the same molecule are typified by the formula A

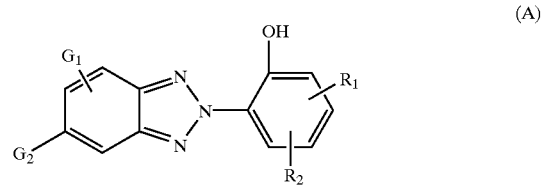

(A)

wherein at least one of $G_2$, $R_1$ or $R_2$ contains a hindered amine moiety are extremely effective light stabilizers having both the UV absorbing activity of a benzotriazole and the light stabilizing efficacy of a hindered amine in the same molecule. These compounds are effective stabilizers for thermoset resin compositions, thermoplastic resin compositions, for photographic applications, for pigmented or dyed polypropylene, polyamide or polyester fibers, and for white, dyed, dipped, unscented and/or scented candle wax against discoloration and fading when incorporated therein alone or in combination with an antioxidant.

2 Claims, No Drawings

BENZOTRIAZOLE/HALS MOLECULAR COMBINATIONS AND COMPOSITIONS STABILIZED THEREWITH

The instant invention pertains to compounds which have a benzotriazole and a hindered amine moiety in the same molecule. These compounds are extremely effective light stabilizers having both the UV absorbing activity of a benzotriazole and the light stabilizing efficacy of a hindered amine in the same molecule. These compounds are effective stabilizers for thermoset resin compositions, for thermoplastic resin compositions, for photographic applications, for pigmented or dyed polypropylene, polyamide or polyester fibers, and for white, dyed, dipped, unscented and/or scented candle wax against discoloration and fading when incorporated therein alone or in combination with an antioxidant.

BACKGROUND OF THE INVENTION

Candles have been known for many centuries going back to the eighth century B.C. The nature of candles is described in Ullmann's Encyclopedia of Industrial Chemistry, Volume A5 at pages 29–30 where it is seen that candles are made from paraffin, beeswax and stearin as basic materials, and where a host of additives may also be present.

It is not surprising that with candles and wax becoming increasingly more important attention was paid as to how to stabilize the said materials. At the National Candle Association Meeting in Houston, 1994, R. van der Vennet presented a paper on "Antioxidants in Wax—Replacement of BHT" touting the use of Vitamin E (tocopherol) as an antioxidant to prevent the yellowing of wax when oxidized. WO 94/13736 describes the same invention.

EP 359,488 A3 and EP 133,964 B1 describe stabilized waxes used in cosmetics where the waxes are the same or similar to those used in candles.

EP 5,922 A1 describes lip cosmetics where the waxes are useful in lipsticks and are related to those useful in candles.

U.S. Pat. No. 5,879,694 describes in detail transparent gel candles both in composition and structure. The use of BHT as an antioxidant is mentioned.

At the National Candle Association Technical Meeting on Apr. 16, 1998, F. A. Ballentine et al., presented a paper entitled "Inhibiting Color Fading of Dyed Candles with CYASORB® Light Absorbers" in which the general theories of thermal oxidation and photodegradation are discussed along with data on the effect of light absorbers on color stability of dyed candle waxes. The light absorbers compared are 4-octyloxy-2-hydroxybenzophenone UV-531; 4-methoxy-2-hydroxybenzophenone UV-9; 2-(2-hydroxy-5-methylphenyl)-2H-benzotriazole UV-5365; 2-(2-hydroxy-5-tert-octylphenyl-2H-benzotriazole UV-5411 and 2-(2-hydroxy-3,5-di-tert-amylphenyl)-2H-benzotriazole UV-2337).

U.S. Pat. No. 5,964,905 teaches dyed and scented candle gels containing triblock copolymers and a hydrocarbon oil of high flash point. This reference teaches that a light (UV) absorber may be used to improve the shelf stability of the candle color when exposed to visible or ultraviolet light. Two preferred absorbers are ethylhexyl p-methoxycinnamate (PARSOL® MCX, Roche) and 2-(2-hydroxy-5-tert-octylphenyl)-2H-benzotriazole (CYASORB® 5411, Cytec).

WO 00/22037 teaches the stabilization of solid, shaped and colored wax articles, including candles, using a malonate UV absorber which may optionally contain a hindered amine moiety as part of the malonate compound structure. The wax articles are dyed with a variety of oil soluble dyes and pigments. The samples protected by dimethyl p-methoxy-benzylidinemalonate exhibited better resistance to discoloration that did samples stabilized with selected benzotriazole or benzophenone UV absorbers.

Japanese Hei 3-278554 teaches that wax crayons (drawing materials) colored by organic pigments can be stabilized by a hindered amine and/or benzotriazole.

In respect to wax stabilization, the use of selected hindered amines and/or benzotriazole UV absorbers is also known in the prior art as seen in U.S. Pat. Nos. 3,530,084; 4,379,721; 4,616,051 and 5,964,905 and copending applications U.S. Ser. Nos. 09/495,495, 09/495,496 and 09/741,583.

Selected compounds which contain both a hindered amine moiety and a benzotriazole moiety in the same molecule are described in U.S. Pat. Nos. 4,289,686 and 5,021,478.

U.S. Pat. Nos. 4,314,933; 4,481,315; 5,278,310; 5,382,588 and 6,166,218; and WO 99/23093 describe other benzotriazole UV absorbers which are related to the instant compounds.

N. Lin et al., Poly. Deg. Stab. 67, 307 (2000) and J. Zakrzewski et al., Poly Deg. Stab. 65, 425 (1999) and ibid, 67, 299 (2000) describe the stabilization of substrates using benzotriazole UV absorbers.

EP 704,560 A1 describes the stabilization of pigmented fibers with a synergistic mixture of hindered amine and UV absorber such as a benzotriazole or s-triazine.

The instant compounds are novel materials and their utility as light stabilizers for thermoset and thermoplastic compositions, for photographic applications and for candle wax is unknown.

OBJECTS OF THE INVENTION

One object of the instant invention is to provide a compound combining in a single molecule a benzotriazole moiety and a hindered amine moiety.

Still another object of the invention is to provide for a white and unscented; white and scented; dyed and unscented; dyed and scented; dipped and unscented; or dipped and scented candle wax stabilized by a compound combining in a single molecule a benzotriazole moiety and a hindered amine moiety alone or in combination with an antioxidant.

Another object of the instant invention is to provide for thermoset compositions stabilized against degradation induced by heat, oxygen or light by incorporation therein an instant compound.

Still another object of the instant invention is to provide for thermoplastic compositions stabilized against degradation induced by heat, oxygen or light by incorporation therein an instant compound.

Another object of this invention is to provide for the stabilization of photographic recording compositions using an instant compound.

Another object of this invention is to provide for the stabilization of dyed or pigmented polypropylene, polyamide or polyester fibers using the instant compounds.

DETAILED DISCLOSURE

The instant invention pertains to a compound of formula A, C or D

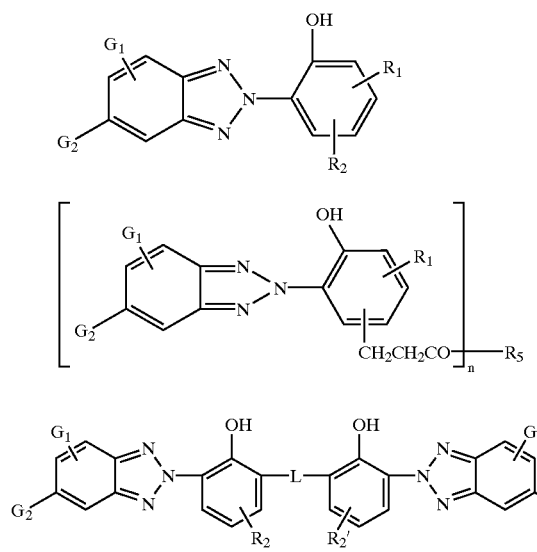

wherein $G_1$ and $G_1'$ are independently hydrogen or halogen, $G_2$ and $G_2'$ are independently hydrogen, halogen, nitro, cyano, $R_3SO-$, $R_3SO_2-$, $-COOG_3$, perfluoroalkyl of 1 to 12 carbon atoms, $-P(O)(C_6H_5)_2$, $-CO-G_3$, $-CO-NH-G_3$, $-CO-N(G_3)_2$, $-N(G_3)-CO-G_3$, phenyl substituted by 2,2,6,6-tetramethylpiperidin-1-yloxy,

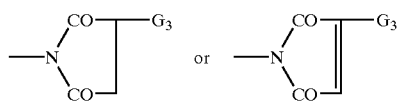

$G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;

or $G_3$ is a group formula I, II or III

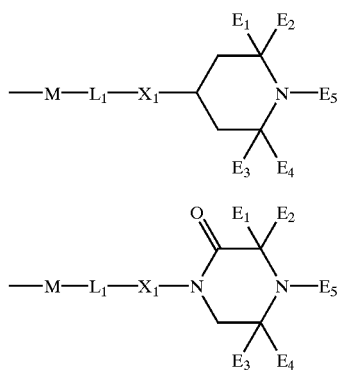

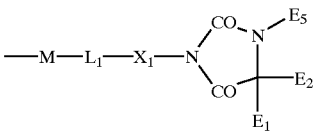

wherein

M is a direct bond, $-NG_9-$, $-O-$, $-S-$, $-SO-$, $-SO_2-$, $-SO_2NG_9-$, $-CONG_9-$, $-COO-$ or $-OCO-$;

$L_1$ is a direct bond, alkylene of 1 to 18 carbon atoms, alkenylene of 3 to 18 carbon atoms, cycloalkylene of 5 to 12 carbon atoms, cycloalkenylene of 5 to 12 carbon atoms or said alkylene interrupted by 1 to 4 oxygen atoms;

$X_1$ is a direct bond, $-COO-$, $-CONG_9-$, $-O-$ or $-NG_9-$;

$G_9$ is hydrogen or alkyl of 1 to 18 carbon atoms;

$E_1$ to $E_4$ are independently alkyl of 1 to 8 carbon atoms, or $E_1$ and $E_2$ together are pentamethylene or $E_3$ and $E_4$ together are pentamethylene;

$E_5$ is hydrogen, oxyl, straight or branched chain alkyl of 1 to 24 carbon atoms, straight or branched chain alkenyl of 3 to 24 carbon atoms, benzyl, acetyl, $-CH_2CH(OH)-E_8$, $-OE_9$, $-OE_{10}(OH)_b$, $E_8$ is hydrogen, methyl, ethyl or phenyl, $E_9$ is hydrogen, straight or branched chain alkyl of 1 to 24 carbon atoms, cycloalkyl of 5 to 12 carbon atoms, straight or branched chain alkenyl of 3 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 15 carbon atoms, aryl of 6 to 10 carbon atoms or said aryl substituted by one to three alkyl of 1 to 4 carbon atoms; or is a group of formula IV

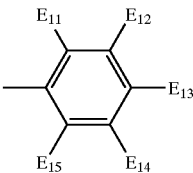

$E_{10}$ is a straight or branched chain alkyl of 1 to 24 carbon atoms, cycloalkyl of 5 to 12 carbon atoms, cycloalkenyl of 5 to 12 carbon atoms, straight or branched chain alkenyl of 3 to 24 carbon atoms, phenylalkyl of 7 to 15 carbon atoms, phenyl or said phenyl substituted by one to three alkyl of 1 to 4 carbon atoms;

b is 1, 2 or 3 with the restriction that b cannot exceed the number of carbon atoms in $E_{10}$, and if b is 2 or 3, each hydroxyl group is attached to a different carbon atom of $E_{10}$;

$E_{11}$ to $E_{15}$ are independently hydrogen, halogen, nitro, cyano, alkyl of 1 to 18 carbon atoms, phenylalkyl of 7 to 15 carbon atoms, aryl of 6 to 10 carbon atoms, hydroxyl, carboxyl, alkylthio of 1 to 18 carbon atoms, alkoxy or 1 to 18 carbon atoms, phenylalkoxy of 7 to 15 carbon atoms, aryloxy of 6 to 10 carbon atoms, alkylcarbonyloxy of 2 to 18 carbon atoms, alkylsulfonyl of 1 to 18 carbon atoms, arylsulfonyl of 6 to 15 carbon atoms, sulfo or phosphono, or any two vicinal substituents connected together to form a mono- or polycyclic ring;

$R_1$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or R$_1$ is a group I, II, III, V or VI

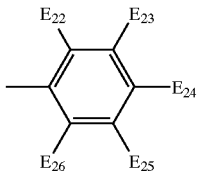
(V)

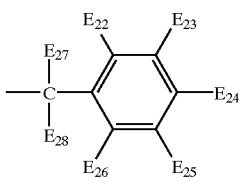
(VI)

where

E$_{27}$ and E$_{28}$ are independently alkyl of 1 to 18 carbon atoms, or cycloalkyl of 5 to 12 carbon atoms;

E$_{22}$, E$_{23}$, E$_{24}$, E$_{25}$ and E$_{26}$ are independently hydrogen, halogen, straight or branched alkyl of 1 to 18 carbon atoms, alkenyl of 2 to 18 carbon atoms, said alkyl or said alkenyl substituted by one or more halogen, —OCOR$_{11}$, —OR$_4$, —NCO, —NHCOR$_{11}$ or —NR$_7$R$_8$, or mixtures thereof, where R$_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NR$_4$— groups or mixtures thereof and which can be unsubstituted or substituted by one or more —OH, —OR$_4$ or —NH$_2$, or mixtures thereof; or E$_{22}$, E$_{23}$, E$_{24}$, E$_{25}$ and E$_{26}$ are independently phenyl, —OH, —OCOR$_{11}$, —OE$_{29}$, —NCO, —NHCOR$_{11}$ or —NR$_7$R$_8$, cyano, nitro, perfluoroalkyl of 1 to 12 carbon atoms, —COG$_3$, —COOG$_3$, —CON(G$_3$)$_2$, —CONHG$_3$, R$_3$S—, R$_3$SO$_2$—, R$_3$SO$_2$—, —P(O)(C$_6$H$_5$)$_2$, —P(O))OG$_3$)$_2$, —SO—X$_2$-E$_{29}$;

X$_2$ is —O—, —NH— or —NR$_4$—;

E$_{29}$ is straight or branched chain alkyl of 1 to 24 carbon atoms, straight or branched chain alkenyl of 2 to 18 carbon atoms, said alkyl or said alkenyl substituted by one or more —OH, —OCOR$_{11}$, —OR$_4$, —NCO, —NHCOR$_{11}$, —NR$_7$R$_8$, phthalimido,

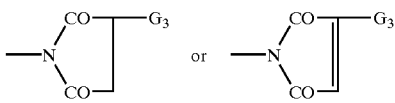

or mixtures thereof, where R$_4$ is straight or branched chain alkyl of 1 to 24 carbon atoms or alkenyl of 2 to 18 carbon atoms; or said alkyl or said alkenyl interrupted by one or more —O—, —NH— or —NR$_4$— groups or mixtures thereof and which can be unsubstituted or substituted by one or more —OH, —OR$_4$ or —NH$_2$, or mixtures thereof; or E$_{29}$ is phenyl or phenylalkyl of 7 to 15 carbon atoms, or said phenyl or said phenylalkyl substituted by one to three alkyl groups of 1 to 4 carbon atoms;

R$_2$ and R$_2$' are independently straight or branched alkyl chain of 1 to 24 carbon atoms, straight or branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 3 alkyl of 1 to 4 carbon atoms; or R$_2$ is hydroxyl or —OR$_4$ where R$_4$ is straight or branched chain alkyl of 1 to 24 carbon atoms; or said alkyl substituted by one or more —OH, —OCO—R$_{11}$, —OR$_4$, —NCO or —NH$_2$ groups or mixtures thereof; or said alkyl or said alkenyl interrupted by one or more —O—, —NH— or —NR$_4$— groups or mixtures thereof and which can be unsubstituted or substituted by one or more —OH, —OR$_4$ or —NH$_2$ groups or mixtures thereof; or R$_2$ and R$_2$' are independently —SR$_3$, —NHR$_3$ or —N(R$_3$)$_2$; or R$_2$ or R$_2$' is a group I, II, III, V or VI defined above;

or R$_2$or R$_2$' is

—(CH$_2$)$_m$—CO—X-(Z)$_p$-Y—R$_{15}$ wherein

X is —O— or —N(R$_{16}$)—,

Y is —O— or —N(R$_{17}$)—,

Z is C$_2$–C$_{12}$-alkylene, C$_4$–C$_{12}$-alkylene interrupted by one to three nitrogen atoms, oxygen atoms or a mixture thereof, or is C$_3$–C$_{12}$-alkylene, butenylene, butynylene, cyclohexylene or phenylene, each substituted by a hydroxyl group, m is zero, 1 or 2, p is 1, or p is also zero when X and Y are —N(R$_{16}$)— and —N(R$_{17}$)—, respectively, R$_{15}$ is a group —CO—C(R$_{18}$)=C(H)R$_{19}$ or, when Y is —N(R$_{17}$)—, forms together with R$_{17}$ a group —CO—CH=CH—CO—, wherein R$_{18}$ is hydrogen or methyl, and R$_{19}$ is hydrogen, methyl or —CO—X—R$_{20}$, wherein R$_{20}$ is hydrogen, C$_1$–C$_{12}$-alkyl or a group of the formula.

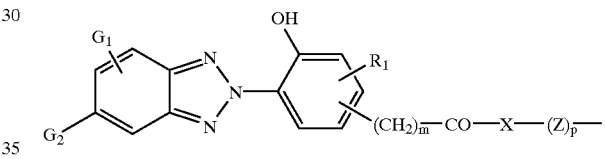

wherein the symbols R$_1$, R$_3$, X, Z, m and p have the meanings defined above, and R$_{16}$ and R$_{17}$ independently of one another are hydrogen, C$_1$–C$_{12}$-alkyl, C$_3$–C$_{12}$-alkyl interrupted by 1 to 3 oxygen atoms, or is cyclohexyl or C$_7$–C$_{15}$aralkyl, and R$_{16}$ together with R$_{17}$ in the case where Z is ethylene, also forms ethylene, n is 1 or 2, when n is 1, R$_5$ is —OR$_6$ or —NR$_7$R$_8$, or R$_5$ is —PO(OR$_{12}$)$_2$, —OSi(R$_{11}$)$_3$ or —OCO—R$_{11}$, a group of formula I, II or III, or straight or branched chain C$_1$–C$_{24}$alkyl which is interrupted by —O—, —S— or —NR$_{11}$ and which can be unsubstituted or substituted by —OH or —OCO—R$_{11}$, C$_5$–C$_{12}$ cycloalkyl which is unsubstituted or substituted by —OH, straight chain or branched C$_2$–C$_{18}$alkenyl which is unsubstituted or substituted by —OH, C$_7$–C$_{15}$aralkyl, —CH$_2$—CHOH—R$_{13}$ or glycidyl, R$_6$ is hydrogen, straight or branched chain C$_1$–C$_{24}$alkyl which is unsubstituted or substituted by one or more OH, OR$_4$ or NH$_2$ groups, or —OR$_6$ is —(OCH$_2$CH$_2$)$_w$OH or —(OCH$_2$CH$_2$)$_w$OR$_{21}$ where w is 1 to 12 and R$_{21}$ is alkyl of 1 to 12 carbon atoms, R$_7$ and R$_8$ are independently hydrogen, alkyl of 1 to 18 carbon atoms, straight or branched chain C$_3$–C$_{18}$alkyl which is interrupted by —O—, —S— or —NR$_{11}$—, C$_5$–C$_{12}$cycloalkyl, C$_6$–C$_{14}$aryl or C$_1$–C$_3$hydroxylalkyl, or R$_7$ and R$_8$ together with the N atom are a pyrrolidine, piperidine, piperazine or morpholine ring, when n is 2, R$_5$ is one of divalent radicals —O—R$_9$—O— or —N(R$_{11}$)—R$_{10}$—N(R$_{11}$)—, R$_9$ is C$_2$–C$_8$alkylene, C$_4$–C$_8$alkenylene, C$_4$alkynylene, cyclohexylene, straight or branched chain C$_4$–C$_{10}$alkylene which is interrupted by —O— or by —CH$_2$—CHOH—CH$_2$—O—R$_{14}$—O—CH$_2$—CHOH—CH$_2$—, R$_{10}$ being straight or branched chain C$_2$–C$_{12}$alkylene which may be interrupted by —O—, cyclohexylene, or

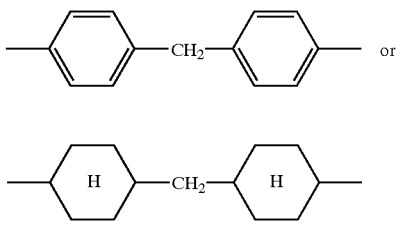

or R$_{10}$ and R$_{11}$ with the two nitrogen atoms form a piperazine ring,

R$_{14}$ is straight or branched chain C$_2$–C$_8$alkylene, straight or branched chain C$_4$–C$_{10}$alkylene which is interrupted by —O—, cycloalkylene, arylene or

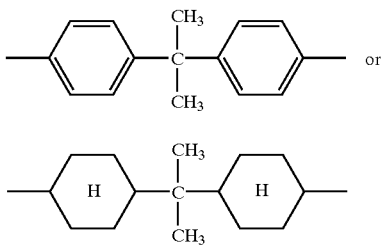

where R$_7$ and R$_8$ are independently hydrogen, alkyl of 1 to 18 carbon atoms or R$_7$ and R$_8$ together are alkylene of 4 to 6 carbon atoms, 3-oxapentamethylene, 3-iminopentamethylene or 3-methyliminopentamethylene, R$_{11}$ is hydrogen, straight or branched chain C$_1$–C$_{18}$alkyl, C$_5$–C$_{12}$cycloalkyl, straight or branched chain C$_3$–C$_8$alkenyl, C$_6$–C$_{14}$aryl or C$_7$–C$_{15}$aralkyl, R$_{12}$ is straight or branched chain C$_1$–C$_{18}$alkyl, straight or branched chain C$_3$–C$_{18}$alkenyl, C$_5$–C$_{10}$cycloalkyl, C$_6$–C$_{16}$aryl or C$_7$–C$_{15}$aralkyl, R$_{13}$ is H, straight chain or branched C$_1$–C$_{18}$alkyl which is substituted by —PO(OR$_{12}$)$_2$, phenyl which is unsubstituted or substituted by OH, C$_7$–C$_{15}$aralkyl or —CH$_2$OR$_{12}$, R$_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, and L is alkylene of 1 to 12 carbon atoms, alkylidene of 2 to 12 carbon atoms, benzylidene, p-xylylene or cycloalkylidene; and with the proviso that at least one of G$_2$, G$_2$', G$_3$, R$_1$, R$_2$ or R$_5$ contains a hindered amine moiety, and with the further provisos that (a) when G$_2$ of formula A is hydrogen or halogen, then E$_5$ of group I is not OE$_9$;

(b) when G$_2$ of formula A is hydrogen or halogen, then E$_5$ of group I is not hydrogen, oxyl, C$_1$–C$_{12}$alkyl, C$_3$–C$_8$alkenyl, benzyl, acetyl, or a group —CH$_2$—CH(OH)-E$_8$;

(c) when G$_2$ is —COOG$_3$ and G$_3$ is of group I, then E$_5$ of group I is not hydrogen, oxyl, C$_1$–C$_{12}$alkyl, C$_3$–C$_8$alkenyl, benzyl, acetyl, or a group —CH$_2$—CH(OH)-E$_8$; and (d) when G$_2$ of formula A is hydrogen, halogen or cyano, then R$_1$ is not a substituted or unsubstituted hydantoin-3-ylmethyl group.

The instant compounds of formula A, C or D include (a) 1-(2-hydroxy-2-methylpropoxy-2,2,6,6-tetramethylpiperidin-4-yl 3-(5-chlorobenzotriazol-2-yl)-5-tert-butyl-4-hydroxyhydrocinnamate;

(b) 5-(1-methoxy-2,2,6,6-tetramethylpiperidin-4-yloxycarbonyl)-2-(2-hydroxy-3-α-cumyl-5-tert-octylphenyl)-2H-benzotriazole;

(c) 1-cyclohexyloxy-2,2,6,6-tetramethylpiperidin-4-yl 3-(5-chlorobenzotriazol-2-yl)-5-tert-butyl-4-hydroxyhydrocinnamate;

(d) 1-methoxy-2,2,6,6-tetramethylpiperidin-4-yl 3-(5-chlorobenzotriazol-2-yl)-5-tert-butyl-4-hydroxyhydrocinnamate;

(e) 1,2,2,6,6-pentamethylpiperidin-4-yl 3-(5-chlorobenzotriazol-2-yl)-5-tert-butyl-4-hydroxyhydrocinnamate;

(f) 2-(1,2,2,6,6-pentamethyl-4-keto-piperazin-5-yl)ethyl 3-(benzotriazol-2-yl)-5-tert-butyl-4-hydroxyhydrocinnamate;

(g) 2-(2,2,6,6-tetramethyl-4-keto-piperazin-5-yl)ethyl 3-(benzotriazol-2-yl)-5-tert-butyl-4-hydroxyhydrocinnamate;

(h) 5-[1-(2-hydroxy-2-methylpropoxy)-2,2,6,6-tetramethylpiperidin-4-yloxy-carbonyl]-2-[2-hydroxy-3-(4-chloro-α,α-dimethylbenzyl)-5-tert-butylphenyl]-2H-benzotriazole;

(i) 2,2,6,6-tetramethylpiperidin-4-yl 3-(benzotriazol-2-yl)-5-tert-butyl-4-hydroxyhydrocinnamate;

(j) 1,2,2,6,6-pentamethylpiperidin-4-yl 3-(benzotriazol-2-yl)-5-tert-butyl-4-hydroxyhydrocinnamate;

(k) 2,2,6,6-tetramethylpiperidin-4-yl 3-(5-phenylsulfonylbenzotriazol-2-yl)-5-tert-butyl-4-hydroxyhydrocinnamate;

(l) 1,2,2,6,6-pentamethylpiperidin-4-yl 3-(5-phenylsulfonylbenzotriazol-2-yl)-5-tert-butyl-4-hydroxyhydrocinnamate;

(m) 1-(2,4-dibromophenoxy)-2,2,6,6-tetramethylpiperidin-4-yl 3-(5-chlorobenzotriazol-2-yl)-5-tert-butyl-4-hydroxyhydrocinnamate;

(n) 1-(2-nitro-4-chlorophenoxy)-2,2,6,6-tetramethylpiperidin-4-yl 3-(5-chlorobenzotriazol-2-yl)-5-tert-butyl-4-hydroxyhydrocinnamate;

(o) 5-trifluoromethyl-2-(2-hydroxy-3-(1,5,5-trimethylhydantoin-3-ylmethyl)-5-tert-butylphenyl-2H-benzotriazole;

(p) 1-cyclohexyloxy-2,2,6,6-tetramethylpiperidin-4-yl 3-(5-chlorobenzotriazol-2-yl)-5-tert-butyl-4-hydroxyhydrocinnamate; or (q) 5-[4-(2,2,6,6-tetramethylpiperidin-1-yloxy)phenyl]-2-(2-hydroxy-3-α-cumyl-5-tert-octylphenyl)-2H-benzotriazole.

The instant invention also pertains to a composition stabilized against thermal, oxidative or light-induced degradation which comprises, (a) an organic material subject to thermal, oxidative or light-induced degradation, and (b) an effective stabilizing amount of a compound of formula A, C or D.

Preferably, the organic material is a natural, semi-synthetic or synthetic polymer, especially a thermoplastic polymer.

Most preferably, the polymer is a polyolefin or polycarbonate, especially polyethylene or polypropylene; most especially polypropylene.

In another preferred embodiment of the instant invention, the organic material is a resin selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol resin crosslinked with melamine containing carbamate groups.

Most preferably, the resin is a thermoset acrylic melamine resin or an acrylic urethane resin.

In yet another preferred embodiment of the instant invention, the organic material is a recording material.

The recording materials according to the invention are suitable for pressure-sensitive copying systems, photocopying systems using microcapsules, heat-sensitive copying systems, photographic materials and ink jet printing.

The recording materials according to the invention are distinguished by an unexpected improvement in quality, especially with regard to the fastness to light.

The recording materials according to the invention have the construction known for the particular use. They consist of a customary carrier, for example, paper or plastic film, which has been coated with one or more layers. Depending on the type of material, these layers contain the appropriate necessary components, in the case of photographic materials, for example, silver halide emulsions, dye couplers, dyes and the like. Material particularly suitable for ink jet printing has a layer particularly absorptive for ink on a customary carrier. Uncoated paper can also be employed for ink jet printing. In this case the paper acts at the same time as the carrier material and as the ink-absorbent layer. Suitable material for ink jet printing is, for example, described in U.S. Pat. No. 5,073,448 which is incorporated herein by reference.

The recording material can also be transparent as, for example, in the case of projection films.

The compounds of formula A, C or D can be incorporated into the carder material as early as the production of the latter, in the production of paper, for example, being added to the paper pulp. A second method of application is to spray the carder material with an aqueous solution of compounds of formula A, C or D, or to add the compounds to the coating composition.

Coating compositions intended for transparent recording materials suitable for projection cannot contain any particles which scatter light, such as pigments and fillers.

The dye-binding coating composition can contain a number of other additives, for example, antioxidants, light stabilizers (including also UV absorbers which do not fall under the scope of the UV absorbers of this invention), viscosity improvers, fluorescent brighteners, biocides and/or antistatic agents.

The coating composition is usually prepared as follows: the water-soluble components, for example, the binder, are dissolved in water and stirred together; the solid components, for example, fillers and other additives already described, are dispersed in this aqueous medium; and disperison is advantageously carried out by means of devices, for example, ultrasonic systems, turbine stirrers, homogenizers, colloid mills, bead mills, sand mills, high-speed stirrers and the like. The compounds of formula A, C or D can be easily incorporated into the coating composition.

The recording material according to this invention preferably contains 1 to 5000 mg/m$^2$, in particular 50–1200 mg/m$^2$, of a compound of formula A, C or D.

As already mentioned, the recording materials according to the invention embrace a wide field. The compounds of formula A, C or D can, for example, be employed in pressure-sensitive copying systems. They can be introduced either into the paper in order to protect the microencapsulated dye precursors there from light, or into the binder of the developer layer in order to protect the dyes formed there.

Photocopying systems using light-sensitive microcapsules which are developed by means of pressure are described in U.S. Pat. Nos. 4,416,966; 4,483,912; 4,352,200; 4,535,050; 4,535,463; 4,551,407; 4,562,137 and 4,608,330; and also in EP-A 139,479; EP-A 162,664; EP-A 164,931; EP-A 237,024; EP-A 237,025 and EP-A 260,129. In all these systems, the compounds can be put into the dye-receiving layer. The compounds can, however, also be put into the donor layer in order to protect the color formers from light.

Photographic materials which can be stabilized are photographic dyes and layers containing such dyes or precursors thereof, for example, photographic paper and films. Suitable materials are, for example, described in U.S. Pat. No. 5,364,749 which is incorporated herein by reference. The compounds of formula A, C or D can act here as a UV filter against electrostatic flashes. In color photographic materials, couplers and dyes are also protected against photochemical decomposition.

The instant compounds can be used for all types of color photographic materials. For example, they can be employed for color paper, color reversal paper, direct-positive color material, color negative film, color positive film, color reversal film and the like. They are preferably used inter alia for photographic color material which contains a reversal substrate or form positives.

Color-photographic recording materials usually contain, on a support, a blue-sensitive and/or a green-sensitive and/or a red-sensitive silver halide emulsion layer and, if desired, a protection layer, with the instant compounds being, preferably, either in the green-sensitive or the red-sensitive layer or in a layer between the green-sensitive and the red-sensitive layer or in a layer on top of the silver halide emulsion layers.

The compounds of formula A, C or D can also be employed in recording materials based on the principles of photopolymerization, photoplasticization or the rupture of microcapsules, or in cases where heat-sensitive and light-sensitive diazonium salts, leuko dyes having an oxidizing agent or dye lactones having Lewis acids are used.

Furthermore, the instant compounds can be employed in recording materials for dye diffusion transfer printing, thermal wax transfer printing and non-matrix printing and for use with electrostatic, electrographic, electrophoretic, magnetographic and laser-electrophotographic printers and pen-plotters. Of the above, recording materials for dye diffusion transfer printing are preferred, for example, as described in EP-A 507,734.

The instant compounds can also be employed in inks, preferably for ink jet printing, for example, as described in U.S. Pat. No. 5,098,477 which is incorporated herein by reference.

The compounds of this invention exhibit superior hydrolytic stability, handling and storage stability as well as good resistance to extractability when present in a stabilized composition.

The methodology to make the instant compounds is described in the prior art. The intermediates needed to make the instant compounds are largely items of commerce.

Preferred compounds are those in which one of X and Y is —O—; and particularly those in which both X and Y are —O—.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, Ia and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

31. Polysiloxanes such as the soft, hydrophilic polysiloxanes described, for example, in U.S. Pat. No. 4,259,467; and the hard polyorganosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsaturated monomers or oligomers and a polyunsaturated aliphatic oligomer.

34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated Monophenols, for Example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated Hydroquinones, for Example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated Thiodiphenyl Ethers, for Example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for Example.
2,2'-methylene-bis-(6-tert-butyl-4-methylphenol)

2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl Compounds, for Example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for Example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for Example,
diphenylamine, N-phenyl-1-naphthylamine, N-(4-tert-octylphenyl)-1-naphthylamine,
4,4'-di-tert-octyl-diphenylamine, reaction product of N-phenylbenzylamine and
2,4,4-trimethylpentene, reaction product of diphenylamine and 2,4,4-trimethylpentene, reaction product of N-phenyl-1-naphthylamine and 2,4,4-trimethylpentene.

2. UV Absorbers and Light Stabilizers
2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1' (1,2-ethanediyl)-bis-(3,3,5,5-tetramethylpiperazinone), bis (1-octyloxy-2,2,6,6-tetramethylpiperidin-4-yl) sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxy-ethoxy)phenyl]-6-(4-chlorophenyl)-s-triazine; 2,4-bis[2-hydroxy-4-(2-hydroxy-4-(2-hydroxy-ethoxy)phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chloro-phenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecyl-pentaerythritol diphosphite, di-(2,4,6-tri-tert-butylphenyl)-pentaerythritol diphosphite, di-(2,4-di-tert-butyl-6-methylphenyl)-pentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. Nos. 4,325,863, 4,338,244 or 5,175,312, or 3-[4-(2-acetoxyethoxy)phenyl]-5,7-di-tert-butyl-benzo-furan-2-one, 5,7-di-tert-butyl-3-[4-(2-stearoyloxyethoxy)phenyl]benzofuran-2-one, 3,3'-bis[5,7-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5, 7-di-tert-butyl-benzofuran-2-one.

The co-stabilizers, with the exception of the benzofuranones listed under 13, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list) and peroxide-destroying compounds (item 5.) of the list.

Additional additives (stabilizers) which are also particularly preferred are benzofuran-2-ones, such as described, for example, in U.S. Pat. Nos. 4,325,863, 4,338,244 or 5,175, 312.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3, 5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxy-benzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3- tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis [2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-1,2,2,6,6-pentamethylpiperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]-undecane)diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]-undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), N-2,2,6,6-tetramethylpiperidin-4-yl-n-dodecylsuccinimide, N-1,2,2,6,6-pentamethylpiperidin-4-yl-n-dodecylsuccinimide, N-1-acetyl-2,2,6,6-tetramethylpiperidin-4-yln-dodecylsuccinimide, 1-acetyl3-dodecyl-7,7,9,9-tetramethyl-1,3,8-triazaspiro[4.5]decane-2,4-dione, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], and 2,4,6-tris[N-(1-cyclohexyloxy-2,2,6,6-tetramethylpiperidin-4-yl)-n-butylamino]-s-triazine.

A most preferred hindered amine compound is bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(1,2,2,6,6-pentamethylpiperidin-4-yl)amino)-s-triazine-2-yl]-1,10-diamino-4,7-diazadecane, di-(1-octyloxy-2,2,6,6-tetramethylpiperidin-4-yl) sebacate, di-(1-cyclohexyloxy-2,2,6,6-tetramethylpiperidin-4-yl) succinate, 1-octyloxy-2,2,6,6-tetramethyl-4-hydroxy-piperidine, poly-{[6-tert-octylamino-s-triazin-2,4-diyl][2-(1-cyclohexyloxy-2,2,6,6-tetramethylpiperidin-4-yl)imino-hexamethylene-[4-(1-cyclohexyloxy-2,2,6,6-tetramethylpiperidin-4-yl)imino], or 2,4,6-tris[N-(1-cyclohexyloxy-2,2,6,6-tetramethylpiperidin-4-yl)-n-butylamino]-s-triazine.

The instant composition can additionally contain another UV absorber selected from the group consisting of the s-triazines, the oxanilides, the hydroxybenzophenones, benzoates and the α-cyanoacrylates.

Particularly, the instant composition may additionally contain an effective stabilizing amount of at least one other 2-hydroxyphenyl-2H-benzotriazole; another tris-aryl-s-triazine; or hindered amine or mixtures thereof.

Preferably, the 2-hydroxyphenyl-2H-benzotriazole is selected from the group consisting of 2-(2-hydroxy-3,5-di-tert-amylphenyl)-2H-benzotriazole;

2-[2-hydroxy-3,5-di(α,α-dimethylbenzyl)phenyl]-2H-benzotriazole;

2-[2-hydroxy-3-(α,α-dimethylbenzyl)-5-octylphenyl]-2H-benzotriazole;

2-{2-hydroxy-3-tert-butyl-5-[2-(omega-hydroxy-octa (ethyleneoxy)carbonyl)ethyl]-phenyl}-2H-benzotriazole; and 2-{2-hydroxy-3-tert-butyl-5-[2-(octyloxy)carbonyl) ethyl]phenyl}-2H-benzotriazole.

Preferably, the other tris-aryl-s-triazine is selected from the group consisting of 2,4-bis(2,4-dimethylphenyl)-6-(2-hydroxy-4-octyloxyphenyl)-s-triazine;

2,4-diphenyl-6-(2-hydroxy-4-hexyloxyphenyl)-s-triazine;

2,4-bis(2,4-dimethylphenyl)-6-[2-hydroxy-4-(3-do-/tridecyloxy-2-hydroxypropoxy)-phenyl]-s-triazine; and 2-(2-hydroxyethylamino)-4,6-bis[N-butyl-N-(1-cyclohexyloxy-2,2,6,6-tetramethylpiperidin-4-yl)amino]-s-triazine.

The alkyd resin lacquers which can be stabilized against the action of light and moisture in accordance with the instant invention are the conventional stoving lacquers which are used in particular for coating automobiles (automobile finishing lacquers), for example lacquers based on alkyd/melamine resins and alkyd/acrylic/melamine resins (see H. Wagner and H. F. Sarx, "Lackkunstharze" (1977), pages 99–123). Other crosslinking agents include glycouril resins, blocked isocyanates or epoxy resins.

The lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

It is also to be noted that the compounds of the present invention are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines and the like. Correspondingly, the epoxide may be utilized as the crosslinking agent for various acrylic or polyester resin systems that have been modified by the presence of reactive groups on the backbone structure.

When used in two-coat finishes, the compounds of the instant invention can be incorporated in the clear coat or both in the clear coat and in the pigmented base coat.

When water-soluble, water miscible or water dispersible coating are desired ammonium salts of acid groups present in the resin are formed. Powder coating composition can be prepared by reacting glycidyl methacrylate with selected alcohol components.

The instant benzotriazoles are made by conventional methods for preparing such compounds. The usual procedure involves the diazotization of a substituted o-nitroaniline followed by coupling the resultant diazonium salt with a substituted phenol and reduction of the azobenzene intermediate to the corresponding desired benzotriazole. The starting materials for these benzotriazoles are largely items of commerce or can be prepared by normal methods of organic synthesis.

While the instant benzotriazoles with their enhanced durability are particularly suited for automotive coating applications, it is contemplated that they will also be especially useful in other applications where their enhanced durability is required such as in solar films and the like.

The instant invention also pertains to a photographic material stabilized against degradation induced by light which comprises
 (a) a photographic material, and
 (b) an effective stabilizing amount of a compound of formula A, C or D as defined above.

The instant invention additionally pertains to a composition stabilized against degradation induced by heat, oxygen or light which comprises
 (a) a thermoset composition, and
 (b) an effective stabilizing amount of a compound of formula A, C or D as defined above.

The thermoset resins of component (a) are selected from the group consisting of a thermoset acrylic melamine resin, an acrylic urethane resin, an epoxy carboxy resin, a silane modified acrylic melamine, an acrylic resin with carbamate pendant groups crosslinked with melamine or an acrylic polyol crosslinked with melamine containing carbamate groups.

The instant invention additionally pertains to a composition stabilized against degradation induced by heat, oxygen or light which comprises
 (a) a thermoplastic composition, and
 (b) an effective stabilizing amount of a compound of formula A, C or D as defined above.

The thermoplastic resin of component (a) includes a polyolefin, polycarbonate, a styrenic, ABS, a polyamide (nylon), a polyester, a polyurethane, a polyacrylate, a polyimide, a rubber modified styrene resin, poly(vinyl chloride), poly(vinyl butyral), polyacetal (polyoxymethylene), or blends or copolymers such as poly(ethylene/1,4-cyclohexylenedimethylene terephthlate) PETG or an ethylene/acrylic acid copolymer of salt thereof (ionomer).

Still another embodiment of the thermoplastic resin is a polyester which is poly(ethylene terephthalate), poly(butylene terephthlate) or poly(ethylene 2,5-naphthalenedicarboxylate) PEN or a copolymer poly (ethylene/1,4-cyclohexylenedimethylene terephthlate) PETG.

Still another embodiment of the thermoplastic resin is a polyolefin which is polyethylene or polypropylene; or is polypropylene.

The thermoplastic resin of component (a) is a polyamide which is poly(m-phenylene isophthalamide), nylon 6 or nylon 66.

The thermoplastic resin of component (a) is a polyimide which is poly(p-phenylene pyromellitimide).

The instant invention additionally pertains to a composition stabilized against degradation induced by heat, oxygen or light which comprises
 (a) dyed or pigmented polypropylene, polyamide or polyester fibers, and
 (b) an effective stabilizing amount of a compound of formula A, C or D, but without the proviso phrases (a), (b), (c) and (d).

One embodiment of the invention is where the fibers of component (a) are pigmented polypropylene fibers.

The instant invention additionally pertains to a composition which comprises
 (a) candle wax which is white and unscented; white and scented; dyed and unscented; dyed and scented; dipped and unscented; or dipped and scented, and
 (b) an effective stabilizing amount of a compound of formula A, C or D, but without the proviso phrases (a), (b), (c) and (d).

The effective stabilizing amount of a compound of formula A, C or D is 0.01 to 10% by weight based on the wax. In another embodiment, the amount of a compound of formula A, C or D is 0.1 to 2% by weight based on the wax; or is 0.1 to 0.5% by weight based on the wax.

Another embodiment is where the effective amount of the compound of formula A, C or D and an antioxidant is 0.1 to 2% by weight based on the wax.

Still another embodiment is where the effective amount of the compound of formula A, C or D and an antioxidant is 0.1 to 0.5% by weight based on the wax.

Examples of the antioxidants useful in this invention are n-octadecyl 3,5-di-tert-butyl-4-hydroxyhydrocinnamate,
 neopentanetetrayl tetrakis(3,5-di-tert-butyl-4-hydroxyhydrocinammate),
 di-n-octadecyl 3,5-di-tert-butyl-4-hydroxybenzylphosphonate,
 1,3,5-tris(3,5-di-tert-butyl-4-hydroxybenzyl) isocyanurate,
 thiodiethylene bis(3,5-di-tert-butyl-4-hydroxyhydrocinnamate),
 1,3,5-trimethyl-2,4,6-tris(3,5-di-tert-butyl-4-hydroxybenzyl)benzene,
 3,6-dioxaoctamethylene bis(3-methyl-5-tert-butyl-4-hydroxyhydrocinnamate),
 2,6-di-tert-butyl-p-cresol,
 2,2'-ethylidene-bis(4,6-di-tert-butylphenol),
 1,3,5-tris(2,6-dimethyl-4-tert-butyl-3-hydroxybenzyl) isocyanurate,
 1,1,3,-tris(2-methyl-4-hydroxy-5-tert-butylphenyl) butane,
 1,3,5-tris[2-(3,5-di-tert-butyl-4-hydroxyhydrocinnamoyloxy)ethyl]isocyanurate,
 3,5-di-(3,5-di-tert-butyl-4-hydroxybenzyl)mesitol,
 hexamethylene bis(3,5-di-tert-butyl-4-hydroxyhydrocinnamate),
 1-(3,5-di-tert-butyl-4-hydroxyanilino)-3,5-di(octylthio)-s-triazine,
 N,N'-hexamethylene-bis(3,5-di-tert-butyl-4-hydroxyhydrocinnamamide),
 calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, N,N-di-($C_{12}$–$C_{24}$alkyl)-N-methyl-amine oxide, or N,N-dialkylhydroxylamine prepared from di(hydrogenated tallow)amine by direct oxidation.

Still other embodiments of antioxidants useful in the instant invention are neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol, or 2,2'-ethylidene-bis(4,6-di-tert-butylphenol).

It should be noted that candles contain a host of various components. The base materials may be made up of the following:

paraffin wax,
natural oils,
polyamide plus fatty acid/ester,
fatty acids such as stearin,
opacifiers,
beeswax,
glycerides plus oxidized wax,
alcohols, and
ethylene oligomers.

Candles also contain a number of additives such as the following:

mold release agents,
fragrances,
insect repellants or insecticides,
hardeners,
crystal modifiers,
clarifiers,
guttering reducers,
colorants,
f.p. control agents,
stretchability improvers,
gelling agents,
extrusion aids, and
vortex reducers.

Each of the various components are meant to control or modify the properties of the candle to insure proper burning, reduce channelling, aid in uniform melting, and the like. The colorants and fragrances obviously are there to provide the proper color, scent or other aesthetic appeal.

Of increasing importance are the transparent gel candles which look like clear glass, but which burn like a classical candle. As is discussed in detail in U.S. Pat. No. 5,879,694, the relevant parts of which are incorporated herein by reference, these gel candles usually contain a copolymer selected from the group consisting of a triblock, radial block, diblock or multiblock copolymer classically made up of at least two thermodynamically incompatible segments containing both hard and soft segments. Typical of such block copolymers is KRATON® (Shell Chemical Co.) which consists of block segments of styrene monomer units and rubber monomer or comonomer units. The most common structure found in KRATON® D series is a linear ABA block with styrene-butadiene-styrene (SBS) or styrene-isoprene-styrene (SIS).

The following examples are meant for illustrative purposes only and are not to be construed to limit the instant invention in any manner whatsoever.

Raw Materials

Wax samples are supplied by the Candle-Lite Corporation. These samples contain dyes and fragrances.

The UV absorbers and hindered amine stabilizers are obtained from the Ciba Speciality Chemicals Corporation except where otherwise specified.

Sample Preparation

The wax samples obtained from the Candle-Lite Corporation already contain a dye and a fragrance (scent). In these cases, the wax is melted and the appropriate stabilizer(s) is (are) added and dissolved in the molten wax. The stabilized wax is then poured into five (5) 44 mm diameter aluminum pans giving five (5) wax disks.

Sample Exposure

Triplicate samples of each disk are exposed under a bank of six (6) cool-white fluorescent lamps (40 watts) or under a bank of six (6) UV lamps having a wavelength of 368 nm with the test samples being twelve (12) inches (30.48 cm) below the lamps.

Dye color fade (or color change) is measured by a Macbeth ColorEye Spectrophotometer with a 6 inch integrating sphere. The conditions are: 10 degree observer; D65 illuminant and 8 degree viewing angle.

Initial color measurements are taken using the above parameters. The L, a and b values are calculated using the CIE system from the reflectance values. YI is calculated from the L, a and b values. Subsequent measurements are taken at specified intervals. Delta L, a, b and YI values are simply the difference between the initial values and the values at each interval. Delta($\Delta$) E is calculated as follows:

$$[(\text{Delta } L)^2 + (\text{Delta } a)^2 + (\text{Delta } b)^2]^{1/2} = \text{Delta } E.$$

EXAMPLE 1

1-(2-Hydroxy-2-methylpropoxy-2,2,6,6-tetramethylpiperidin-4-yl 3-(5-Chlorobenzotriazol-2-yl)-5-tert-butyl-4-hydroxyhydrocinnamate Xylenes (130.5 g, 1.23 mols), methyl 3-(5-chlorobenzotriazol-2-yl)-5-tert-butyl-4-hydroxyhydrocinnamate (7.95 g, 0.021 mol) and 1-(2-hydroxy-2-methylpropoxy-2,2,6,6-tetramethyl-4-hydroxypiperidine (5.81 g, 0.024 mol) are charged to a reactor and heated to reflux. After drying for 1.5 hours, lithium amide (0.32 g, 0.0139 mol) is charged to the reactor and reflux is continued for four hours. The reaction mass is then cooled and 300 mL of ethyl acetate is added. The solution is clarified and the solvent is removed by distillation giving 17.43 g of crude product. The crude product is dissolved in heptane/ethyl acetate (98/2) and chromatographed on silica gel. The title compound is obtained in a yield of 7.71 g (63%) as a yellow solid melting at 150–158° C. whose structure is consistent with $^1$Hnmr and mass spectrometry. The molar absorptivity of the compound is 15,890 l/mole cm.

EXAMPLE 2

5-(1-Methoxy-2,2,6,6-tetramethylpiperidin-4-yloxycarbonyl)-2-(2-hydroxy-3-α-cumyl-5-tert-octylphenyl)-2H-benzotriazole 5-(1-Methoxycarbonyl)-2-(2-hydroxy-3-α-cumyl-5-tert-octylphenyl)-2H-benzotriazole (2.56 g, 0.0051 g) and 1-methoxy-2,2,6,6-tetramethyl-4-hydroxypiperidine (1.29 g, 0.0069 mol) are reacted under the conditions given in Example 1. The title compound is obtained as a yellow solid, melting at 84–90° C., in a yield of 3.3 g (99%) whose structure is consistent with ¹Hnmr and mass spectrometry. The molar absorptivity of the compound is 16,192 l/mole cm.

EXAMPLE 3

1-Cyclohexyloxy-2,2,6,6-tetramethylpiperidin-4-yl 3-(5-Chlorobenzotriazol-2-yl)-5-tert-butyl-4-hydroxyhydrocinnamate Toluene (215 g, 2.34 mols), 3-(5-chlorobenzotriazol-2-yl)-5-tert-butyl-4-hydroxyhydrocinnamic acid (12.82 g, 0.034 mol), 1-(2-cyclohexyloxy-2,2,6,6-tetramethyl-4-hydroxypiperidine (8.77 g, 0.34 mol), dicyclohexylcarbodiimide (12.78 g, 0.062 mol) and dimethylaminopyridine (0.95 g, 0.0078 mol) are charged to a lab reactor and heated to 75–85° C. The reaction mass is held at this temperature for twenty hours. The reaction mass is then cooled to ambient temperature and 200 mL of ethyl acetate is added. The mixture is then clarified through filter paper. The solvent is removed by distillation. The crude product obtained is redissolved in heptane/ethyl acetate (96/4) and chromatographed on silica gel. The title compound is obtained in a yield of 7.24 g (34.5%) as a light yellow solid, melting at 130–136° C., whose structure is consistent with ¹Hnmr and mass spectrometry. The compound has a molar absorptivity of 14,925 l/mole cm.

EXAMPLE 4

1-Methoxy-2,2,6,6-tetramethylpiperidin-4-yl 3-(5-Chlorobenzotriazol-2-yl)-5-tert-butyl-4-hydroxyhydrocinnamate 3-(5-Chlorobenzotriazol-2-yl)-5-tert-butyl-4-hydroxyhydrocinnamic acid (12.0 g, 0.032 mol) and 1-methoxy-2,2,6,6-tetramethyl-4-hydroxypiperidine (6.66 g, 0.036 mol) are reacted together according to the procedure given in Example 3. The title compound is obtained in a yield of 8.79 g (50.5%) as a light yellow solid, melting at 132–137° C., whose structure is consistent with ¹Hnmr and mass spectrometry. The compound has a molar absorptivity of 17,210 l/mole cm.

EXAMPLE 5

1,2,2,6,6-Pentamethylpiperidin-4-yl 3-(5-Chlorobenzotriazol-2-yl)-5-tert-butyl-4-hydroxyhydrocinnamate Methyl 3-(5-chlorobenzotriazol-2-yl)-5-tert-butyl-4-hydroxyhydrocinnamate (10.0 g, 0.026 mol) and 1,2,2,6,6-pentamethyl-4-hydroxypiperidine (3.98 g, 0.023 mol) are reacted together according to the procedure of Example 1. The title compound is obtained in a yield of 3.23 g (26%) as an off-white solid, melting at 150–158° C., whose structure is consistent with ¹Hnmr and mass spectrometry. The compound has a molar absorptivity of 17,092 l/mole cm.

EXAMPLE 6

2-(1,2,2,6,6-Pentamethyl-4-keto-piperazin-5-yl)ethyl 3-(Benzotriazol-2-yl)-5-tert-butyl-4-hydroxyhydrocinnamate Xylenes (30.1 g, 0.28 mol), methyl 3-(benzotriazol-2-yl)-5-tert-butyl-4-hydroxyhydrocinnamate (7.76 g, 0.022 mol), 2-(1,2,2,6,6-pentamethyl-4-keto-piperazin-5-yl)-ethanol (4.96 g, 0.023 mol) and tin 2-ethylhexanoate are added to a laboratory reactor. The solution is refluxed for six hours. The xylene is then removed by distillation under vacuum. The hot oily product obtained is crystallized from 150 mL of heptane and recrystallized from 120 mL of isopropanol. The title compound is obtained in a yield of 9.7 g (83%) as an off-white solid, melting at 102–104° C., whose structure is consistent with ¹Hnmr and mass spectrometry.

EXAMPLE 7

2-(2,2,6,6-Tetramethyl-4-keto-piperazin-5-yl)ethyl 3-(Benzotriazol-2-yl)-5-tert-butyl-4-hydroxyhydrocinnamate Methyl 3-(benzotriazol-2-yl)-5-tert-butyl-4-hydroxyhydrocinnamate (8.38 g, 0.024 mol) and 2-(2,2,6,6-tetramethyl-4-keto-piperazin-5-yl)ethanol (5.0 g, 0.025 mol) are reacted together according to the procedure of Example 6. The title compound is obtained in a yield of 8.4 g (67%) as an off-white solid, melting at 124–125° C., whose structure is consistent with ¹Hnmr and mass spectrometry.

EXAMPLE 8

5-[1-(2-Hydroxy-2-methylpropoxy)-2,2,6,6-tetramethylpiperidin-4-yloxycarbonyl]-2-[2-hydroxy-3-(4-chloro-α,α-dimethylbenzyl)-5-tert-butylphenyl]-2H-benzotriazole 5-Methoxycarbonyl2-[2-hydroxy-3-(4-chloro-α,α-dimethylbenzyl)-5-tert-butyl-phenyl]-2H-benzotriazole (3.89 g, 0.0081 mol) and 1-(2-hydroxy-2-methylpropoxy)-2,2,6,6-tetramethyl-4-hydroxypiperidine (2.41 g, 0.0098 mol) are reacted together according to the procedure of Example 1. The title compound is obtained in a yield of 2.26 g (40.2%) as a yellow solid, melting at 80–90° C., whose structure is consistent with ¹Hmnr and mass spectrometry. The compound has a molar absorptivity of 17,411 l/mole cm.

EXAMPLE 9

2,2,6,6-Tetramethylpiperidin-4-yl 3-(Benzotriazol-2-yl)-5-tert-butyl-4-hydroxyhydrocinnamate This compound is prepared according to the method of Example 1a of U.S. Pat. No. 4,289,686.

EXAMPLE 10

1,2,2,6,6-Pentamethylpiperidin-4-yl 3-(Benzotriazol-2-yl)-5-tert-butyl-4-hydroxyhydrocinnamate This compound is prepared according to the method of Example 1b of U.S. Pat. No. 4,289,686.

EXAMPLE 11

2,2,6,6-Tetramethylpiperidin-4-yl 3-(5-phenylsulfonylbenzotriazol-2-yl)-5-tert-butyl-4-hydroxyhydrocinnamate Methyl 3-(5-phenylsulfonylbenzotriazol-2-yl)-5-tert-butyl-4-hydroxyhydrocinnamate (10 g, 0.02 mol), xylenes (100 g, 0.93 mol) and 2,2,6,6-tetramethyl-4-hydroxypiperidine (4.0 g, 0.025 mol) are charged to a reactor. The contents are heated to reflux in order to dry the xylenes. The contents are cooled to 50° C. at which time lithium amide (0.4 g, 0.017 mol) is added. The reaction mass is then heated to reflux and held at that temperature for 3.5 hours. The reaction is monitored by thin layer chromatography. The reaction mass is cooled to 50° C. and washed thrice with 100 g of water. The xylene is removed by distillation under vacuum to give 12.8 g of an orange oil which is subjected to silica gel chromatography for purification using ethyl acetate as the eluent. The title compound is obtained in a yield of 9.6 g (77%) as a yellow semi-solid, melting at 85–125° C., whole structure is confirmed by mass spectrometry and $^1$Hnmr.

EXAMPLE 12

1,2,2,6,6-Pentamethylpiperidin-4-yl 3-(5-Phenylsulfonylbenzotriazol-2-yl)-5-tert-butyl-4-hydroxyhydrocinnamate Methyl 3-(5-phenylsulfonylbenzotriazol-2-yl)-5-tert-butyl-4-hydroxyhydrocinnamate (5 g, 0.01 mol), xylenes (18 g, 0.17 mol), 1,2,2,6,6-pentamethyl-4-hydroxypiperidine (2.1 g, 0.012 mol) and dioctyltin oxide (0.5 g, 0.0014 mol) are charged to a reactor and heated to 160° C. while being vigorously stirred. At the end of six hours, any remaining xylene is removed by distillation under vacuum. The crude yellow oil obtained is chromatographed through a pad of silica gel using ethyl aetate as the eluent. The title compound is obtained in a 70% yield as a low melting yellow solid, melting at 45–52° C., whose structure is consistent with $^1$Hnmr and mass spectrometry.

EXAMPLE 13

1-(2,4-Dibromophenoxy)-2,2,6,6-tetramethylpiperidin-4-yl 3-(5-Chlorobenzotriazol-2-yl)-5-tert-butyl-4-hydroxyhydrocinnamate The title compound is prepared according to the procedure of Example 3 using 3-(5-chlorobenzotriazol-2-yl)-5-tert-butyl-4-hydroxyhydrocinnamic acid and 1-(2,4-dibromophenoxy)-2,2,6,6-tetramethyl-4-hydroxypiperidine.

EXAMPLE 14

1-(2-Nitro-4-chlorophenoxy)-2,2,6,6-tetramethylpiperidin-4-yl 3-(5-Chlorobenzotriazol-2-yl)-5-tert-butyl-4-hydroxyhydrocinnamate The title compound is prepared according to the procedure of Example 3 using 3-(5-chlorobenzotriazol-2-yl)-5-tert-butyl-4-hydroxyhydrocinnamic acid and 1-(2-nitro-4-chloro-phenoxy)-2,2,6,6-tetramethyl-4-hydroxypiperidine.

EXAMPLE 15

5-Trifluoromethyl-2-(2-hydroxy-3-(1,5,5-trimethylhydantoin-3-ylmethyl)-5-tert-butylphenyl-2H-benzotriazole The title compound is prepared by the reaction of 5-trifluoromethyl-2-(2-hydroxy-5-tert-butylphenyl-2H-benzotriazole and 1,5,5-trimethylhydantoin as shown in WO 99/23093.

EXAMPLE 16

1-Cyclohexyloxy-2,2,6,6-tetramethylpiperidin-4-yl 3-(5-Chlorobenzotriazol-2-yl)-5-tert-butyl-4-hydroxyhydrocinnamate This compound is prepared according to the method of Example 2 of U.S. Pat. No. 5,021,478.

EXAMPLE 17

5-(4-Aminophenyl)-2-(2-hydroxy-3-α-cumyl-5-tert-octylphenyl)-2H-benzotriazole

Into a mixture of 5.21 g (10 mmol) of 5-bromo-2-(2-hydroxy-3-α-cumyl-5-tert-octylphenyl-2H-benzotriazole, 2.29 g (10.5 mmol) of 4-(4,4,5,5-tetramethyl-1,3,2-dioxoborolan-2-yl)aniline is added 250 mL of n-propanol. The reaction mixture is then evacuated and filled with nitrogen three times followed by the addition of a mixture of 0.09 g (0.4 mmol) of palladium acetate, 0.32 g (1.2 mmol) of triphenylphosphine, 6 mL of 2M solution of sodium carbonate and 10 mL of distilled water. The reaction mixture is then evacuated and filled with nitrogen three times. After stirring at ambient temperature for ten minutes, the reaction mixture is heated to 85–90° C. Within a half hour, the reaction mixture changes from a light orange color to red and becomes completely dark in one hour. After an additional hour of heating, the reaction mixture is allowed to cool to ambient temperature. The residual catalyst is removed by filtration and the filtrate is concentrated to a dark brown solid which is purified by dry column flash chromatography (toluene eluent) to give 4.45 g of a crystalline solid in 83.5% yield. MS [M+1] 533.

EXAMPLE 18

5-[4-(2,2,6,6-Tetramethylpiperidin-1-yloxy)-phenyl]-2-(2-hydroxy-3-α-cumyl-5-tert-octylphenyl)-2H-benzotriazole The title compound is prepared reacting 0.59 g (3.75 mmol) of 1-oxyl-2,2,6,6-tetramethylpiperidine, 1.0 g (10 mmol) of tert-butyl nitrite, 2.3 mg (0.0037 mmol) of (S,S)-(+)-N,N-bis(3,5-di-tert-butylsalicylidene)-1,2-cyclohexanediaminocobalt(II), 120 mL of pyridine and 24.0 g (75 mmol) of 5-(4-aminophenyl)-2-(2-hydroxy-3-α-cumyl-5-tert-octylphenyl)-2H-benzotriazole, prepared in Example 17, in 10 mL of pyridine at 70° C. The crude product obtained is purified by vacuum flash chromatography (2% ethyl acetate/heptane) to give 2.20 g of the title compound as a colorless oil in 87.3% yield. M/S [M+1] 673.

EXAMPLE 19

Color Fade of Blue Scented Candle Wax under Fluorescent Lamp Exposure

A variety of different stabilizers are evaluated in blue scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 63 days |
| --- | --- |
| Blank (no add) | 9.16 |
| A (0.3%) | 5.96 |
| B (0.15%) + C (0.15%) | 3.68 |
| A (0.15%) + D (0.15%) | 2.77 |
| Example 5 (0.3%) | 2.75 |
| Example 4 (0.3%) | 2.10 |
| Example 11 (0.3%) | 1.94 |

-continued

| Sample* (wt % add) | ΔE after 63 days |
|---|---|
| Example 1 (0.3%) | 1.81 |
| Example 2 (0.3%) | 1.71 |
| Example 16 (0.3%) | 1.57 |
| Example 3 (0.3%) | 1.44 |
| Example 10 (0.3%) | 1.33 |
| Example 9 (0.3%) | 1.21 |
| Example 8 (0.3%) | 1.04 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1-octyloxy-2,2,6,6-tetramethylpiperidin-4-yl) sebacate, TINUVIN ® 123, CIBA.

These data show that an instant compound of Example 1–5, 8–11 or 16 protects the blue scented candle wax from unwanted discoloration far better than do conventional stabilizer systems.

EXAMPLE 20

Color Fade of Blue Scented Candle Wax under UV Lamp Exposure

A variety of different stabilizers are evaluated in blue scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 13 days |
|---|---|
| Blank (no add) | 17.11 |
| A (0.3%) | 6.14 |
| B (0.15%) + C (0.15%) | 7.54 |
| A (0.15%) + D (0.15%) | 3.36 |
| Example 8 (0.3%) | 3.27 |
| Example 2 (0.3%) | 3.17 |
| Example 4 (0.3%) | 2.77 |
| Example 11 (0.3%) | 2.26 |
| Example 1 (0.3%) | 2.03 |
| Example 16 (0.3%) | 1.94 |
| Example 5 (0.3%) | 1.86 |
| Example 3 (0.3%) | 1.85 |
| Example 10 (0.3%) | 1.44 |
| Example 9 (0.3%) | 1.03 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1-octyloxy-2,2,6,6-tetramethylpiperidin-4-yl) sebacate, TINUVIN ® 123, CIBA.

These data show that an instant compound of Example 1–5, 8–11 or 16 protects the blue scented candle wax from unwanted discoloration far better than do conventional stabilizer systems.

EXAMPLE 21

Color Fade of Gray Scented Candle Wax under Fluorescent Lamp Exposure

A variety of different stabilizers are evaluated in gray scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 70 days |
|---|---|
| Blank (no add) | 21.16 |
| A (0.3%) | 12.58 |
| A (0.5%) | 12.15 |
| B (0.15%) + C (0.15%) | 14.45 |
| A (0.15%) + D (0.15%) | 4.93 |
| Example 1 (0.3%) | 4.32 |
| Example 11 (0.3%) | 4.11 |
| Example 3 (0.3%) | 3.74 |
| Example 16 (0.3%) | 3.50 |
| Example 4 (0.3%) | 3.36 |
| Example 2 (0.3%) | 3.08 |
| Example 10 (0.3%) | 2.91 |
| Example 8 (0.3%) | 2.62 |
| Example 9 (0.3%) | 2.60 |
| Example 5 (0.3%) | 2.39 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1-octyloxy-2,2,6,6-tetramethylpiperidin-4-yl) sebacate, TINUVIN ® 123, CIBA.

These data show that an instant compound of Example 1–5, 8–11 or 16 protects the gray scented candle wax from unwanted discoloration far better than do conventional stabilizer systems.

EXAMPLE 22

Color Fade of Gray Scented Candle Wax under UV Lamp Exposure

A variety of different stabilizers are evaluated in gray scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 70 days |
|---|---|
| Blank (no add) | 42.22 |
| A (0.3%) | 15.86 |
| B (0.15%) + C (0.15%) | 20.21 |
| A (0.15%) + D (0.15%) | 7.45 |
| Example 4 (0.3%) | 5.14 |
| Example 5 (0.3%) | 5.10 |
| Example 2 (0.3%) | 4.97 |
| Example 8 (0.3%) | 4.67 |
| Example 10 (0.3%) | 4.56 |
| Example 3 (0.3%) | 4.55 |

-continued

| Sample* (wt % add) | ΔE after 70 days |
|---|---|
| Example 9 (0.3%) | 4.49 |
| Example 1 (0.3%) | 4.48 |

*A is cotyl 3-(benzotriazol-2-yl)-5-tert-butyl-4-hydroxyhydroxinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1-octyloxy-2,2,6,6-tetramethylpiperidin-4-yl) sebacate, TINU-VIN ® 123, CIBA.

These data show that an instant compound of Example 1–5 or 8–10 protects the gray scented candle wax from unwanted discoloration far better than do conventional stabilizer systems.

EXAMPLE 23

Color Fade of Green Scented Candle Wax under Fluorescent Lamp Exposure

A variety of different stabilizers are evaluated in green scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 28 days |
|---|---|
| Blank (no add) | 8.74 |
| A (0.3%) | 7.08 |
| B (0.15%) + C (0.15%) | 6.81 |
| A (0.15%) + D (0.15%) | 6.26 |
| Example 8 (0.3%) | 6.06 |
| Example 11 (0.3%) | 5.95 |
| Example 9 (0.3%) | 5.49 |
| Example 10 (0.3%) | 5.47 |
| Example 2 (0.3%) | 5.03 |
| Example 4 (0.3%) | 4.84 |
| Example 3 (0.3%) | 4.00 |
| Example 1 (0.3%) | 2.62 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1-octyloxy-2,2,6,6-tetramethylpiperidin-4-yl) sebacate, TINU-VIN ® 123, CIBA.

These data show that an instant compound of Example 1–4 or 8–11 protects the green scented candle wax from unwanted discoloration far better than do conventional stabilizer systems.

EXAMPLE 24

Color Fade of Green Scented Candle Wax under UV Lamp Exposure

A variety of different stabilizers are evaluated in green scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 42 days |
|---|---|
| Blank (no add) | 17.22 |
| A (0.3%) | 10.17 |
| A (0.15%) + D (0.15%) | 12.15 |
| Example 4 (0.3%) | 9.90 |
| Example 9 (0.3%) | 9.69 |
| Example 3 (0.3%) | 8.91 |
| Example 5 (0.3%) | 8.77 |
| Example 1 (0.3%) | 6.59 |

*A is octyl 3-(benzotriazol-2-yl)-5-tert-butyl-4-hydroxyhydrocinnamate, TINUVIN ® 384, CIBA.
B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
D is bis(1-octyloxy-2,2,6,6-tetramethylpiperidin-4-yl) sebacate, TINU-VIN ® 123, CIBA.

These data show that an instant compound of Example 1, 3–5 or 9 protects the green scented candle wax from unwanted discoloration far better than do conventional stabilizer systems.

EXAMPLE 25

Color Fade of Pink Scented Candle Wax under Fluorescent Lamp Exposure

A variety of different stabilizers are evaluated in pink scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 19 days |
|---|---|
| Blank (no add) | 14.71 |
| F (0.3%) | 9.30 |
| G (0.3%) | 10.79 |
| B (0.15%) + C (0.15%) | 6.13 |
| F (0.15%) + E (0.15%) | 7.94 |
| Example 3 (0.3%) | 6.12 |
| Example 1 (0.3%) | 6.15 |
| Example 10 (0.3%) | 5.12 |

*B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is bis(1,2,2,6,6-pentamethylpiperidin-4-yl) sebacate, TINUVIN ® 292, CIBA.
F is dimethyl p-methoxybenzylidenemalonate, SANDUVOR ® PR 25, Clariant.
G is di(1,2,2,6,6-penta methylpiperidin-4-yl) p-methoxybenzylidenemalonate, SANDUVOR ® PR 31, Clariant.

These data show that an instant compound of Example 1, 3 or 10 protects the pink scented candle wax from unwanted discoloration far better than do conventional stabilizer systems including prior art malonate UV absorbers, even a malonate ester containing a hindered amine moiety.

EXAMPLE 26

Color Fade of Pink Scented Candle Wax under UV Lamp Exposure

A variety of different stabilizers are evaluated in pink scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 19 days |
|---|---|
| Blank (no add) | 18.98 |
| F (0.3%) | 21.47 |
| G (0.3%) | 16.31 |
| B (0.15%) + C (0.15%) | 7.78 |
| F (0.15%) + E (0.15%) | 14.54 |
| Example 10 (0.3%) | 3.79 |
| Example 1 (0.3%) | 3.53 |
| Example 3 (0.3%) | 3.32 |

*B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is bis(1,2,2,6,6-pentamethylpiperidin-4-yl) sebacate, TINUVIN ® 292, CIBA.
F is dimethyl p-methoxybenzylidenemalonate, SANDUVOR ® PR 25, Clariant.
G is di(1,2,2,6,6-penta methylpiperidin-4-yl) p-methoxybenzylidenemalonate, SANDUVOR ® PR 31, Clariant.

These data show that an instant compound of Example 1, 3 or 10 protects the pink scented candle wax from unwanted discoloration far better than do conventional stabilizer systems including prior art malonate UV absorbers, even a malonate ester containing a hindered amine moiety.

EXAMPLE 27

Color Fade of Gray Scented Candle Wax under Fluorescent Lamp Exposure

A variety of different stabilizers are evaluated in gray scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 33 days |
|---|---|
| Blank (no add) | 19.02 |
| F (0.3%) | 17.31 |
| G (0.3%) | 8.68 |
| B (0.15%) + C (0.15%) | 14.44 |
| F (0.15%) + E (0.15%) | 6.98 |
| Example 3 (0.3%) | 5.05 |
| Example 10 (0.3%) | 4.66 |
| Example 3 (0.3%) | 5.32 |

*B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is bis(1,2,2,6,6-pentamethylpiperidin-4-yl) sebacate, TINUVIN ® 292, CIBA.
F is dimethyl p-methoxybenzylidenemalonate, SANDUVOR ® PR 25, Clariant.
G is di(1,2,2,6,6-penta methylpiperidin-4-yl) p-methoxybenzylidenemalonate, SANDUVOR ® PR 31, Clariant.

These data show that an instant compound of Example 1, 3 or 10 protects the gray scented candle wax from unwanted discoloration far better than do conventional stabilizer systems including prior art malonate UV absorbers, even a malonate ester containing a hindered amine moiety.

EXAMPLE 28

Color Fade of Gray Scented Candle Wax under UV Lamp Exposure

A variety of different stabilizers are evaluated in gray scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 17 days |
|---|---|
| Blank (no add) | 34.09 |
| F (0.3%) | 29.81 |
| G (0.3%) | 24.77 |
| B (0.15%) + C (0.15%) | 14.34 |
| F (0.15%) + E (0.15%) | 25.78 |
| B (0.15%) + E (0.15%) | 6.06 |
| Example 10 (0.3%) | 5.09 |
| Example 3 (0.3%) | 5.04 |
| Example 1 (0.3%) | 4.73 |

*B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is bis(1,2,2,6,6-pentamethylpiperidin-4-yl) sebacate, TINUVIN ® 292, CIBA.
F is dimethyl p-methoxybenzylidenemalonate, SANDUVOR ® PR 25, Clariant.
G is di(1,2,2,6,6-penta methylpiperidin-4-yl) p-methoxybenzylidenemalonate, SANDUVOR ® PR 31, Clariant.

These data show that an instant compound of Example 1, 3 or 10 protects the gray scented candle wax from unwanted discoloration far better than do conventional stabilizer systems including prior art malonate UV absorbers, even a malonate ester containing a hindered amine moiety.

EXAMPLE 29

Color Fade of White Scented Candle Wax under Fluorescent Lamp Exposure

A variety of different stabilizers are evaluated in white scented candle wax obtained from the Candle-Lite Corporation under fluorescent lamp exposure. The ΔE values represent the change in color after the indicated days of exposure. A low ΔE value indicates less change in color and is highly desired.

| Sample* (wt % add) | ΔE after 19 days |
|---|---|
| Blank (no add) | 37.21 |
| F (0.3%) | 30.29 |
| G (0.3%) | 26.39 |
| B (0.15%) + C (0.15%) | 23.91 |
| F (0.15%) + E (0.15%) | 27.57 |
| B (0.15%) + E (0.15%) | 25.10 |

-continued

| Sample* (wt % add) | ΔE after 19 days |
|---|---|
| Example 3 (0.3%) | 5.97 |
| Example 1 (0.3%) | 5.23 |

*B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is bis(1,2,2,6,6-pentamethylpiperidin-4-yl) sebacate, TINUVIN ® 292, CIBA.
F is dimethyl p-methoxybenzylidenemalonate, SANDUVOR ® PR 25, Clariant.
G is di(1,2,2,6,6-penta methylpiperidin-4-yl) p-methoxybenzylidenemalonate, SANPUVOR ® PR 31, Clariant.

These data show that an instant compound of Example 1 or 3 protects the white scented candle wax from unwanted discoloration far better than do conventional stabilizer systems including prior art malonate UV absorbers, even a malonate ester containing a hindered amine moiety. Indeed, the instant compound of Example 1 or 3 appears to provide orders of magnitude better stabilization than the prior art systems.

EXAMPLE 30

Color Fade of White Scented Candle Wax under UV Lamp Exposure

A variety of different stabilizers are evaluated in white scented candle wax obtained from the Candle-Lite Corporation under UV lamp exposure. The ΔE values represent the change in color after the indicated days of exposure. A low ΔE value indicates less change in color and is highly desired.

| Sample* (wt % add) | ΔE after 19 days |
|---|---|
| Blank (no add) | 42.98 |
| F (0.3%) | 39.29 |
| G (0.3%) | 25.10 |
| B (0.15%) + C (0.15%) | 26.07 |
| F (0.15%) + E (0.15%) | 25.49 |
| B (0.15%) + E (0.15%) | 25.74 |
| Example 3 (0.3%) | 7.66 |
| Example 1 (0.3%) | 7.06 |

*B is 2-(2-hydroxy-5-tert-octylphenyl)-2H-benzotriazole, TINUVIN ® 329, CIBA.
C is 4-octyloxy-2-hydroxybenzophenone, CHIMMASORB ® 81, CIBA.
E is bis(1,2,2,6,6-pentamethylpiperidin-4-yl) sebacate, TINUVIN ® 292, CIBA.
F is dimethyl p-methoxybenzylidenemalonate, SANDUVOR ® PR 25, Clariant.
G is di(1,2,2,6,6-penta methylpiperidin-4-yl) p-methoxybenzylidenemalonate, SANPUVOR ® PR 31, Clariant.

These data show that an instant compound of Example 1 or 3 protects the white scented candle wax from unwanted discoloration far better than do conventional stabilizer systems including prior art malonate UV absorbers, even a malonate ester containing a hindered amine moiety. Indeed, the instant compound of Example 1 or 3 appears to provide orders of magnitude better stabilization than the prior art systems.

EXAMPLE 31

Stabilization of a Photographic Layer

Chromogenic photographic layers are prepared by coating a gelatine emulsion containing silver bromide, a yellow coupler and an additive on a polyethylene-coated paper.

The composition of the layers is as given in the table below with all amounts in mg/m².

| Component | Amount in the layer |
|---|---|
| gelatine | 5150 |
| silver bromide | 520 |
| yellow coupler* | 973 |
| coupler solvent** | 324 |
| additive | 250 |
| hardener*** | 300 |
| surfactant**** | 340 |

*Kodak Coupler
**di-n-butyl phthalate
***2-hydroxy-4,6-dichloro-s-triazine
****4,8-di-sec-butylnaphthalene-2-sulfonate, sodium salt The layers are dried for seven days in a ventilated cabinet.

The dried samples are exposed to white light through a step wedge of 0.3 log E exposure steps and then developed with Agfa's P94 process for color negative papers following the manufacturer's recommendations.

After exposure and processing, the remission density of the yellow dye is measured in the blue channel. The samples are then exposed in an Atlas Weather-Ometer so as to received 120 kJ/cm² light energy. The temperature is 43° C. and the relative humidity is 50%. The density loss starting from a density of 1 is determined as seen in the table below.

| Additive Compound of | Density loss (%) |
|---|---|
| None | 57 |
| Example 2 | 45 |
| Example 1 | 40 |
| Example 8 | 40 |

These data show that the instant compounds provide excellent light stabilization efficacy for the yellow dye in this photographic application.

EXAMPLE 32

Incorporation into Photographic Layers

A gelatin coat of the following composition (per m²) is applied in the customary manner to a polyester base.

| Components | Amount |
|---|---|
| Gelatin | 1200 mg |
| Tricresyl Phosphate | 510 mg |
| Hardener* | 40 mg |
| Wetting Agent** | 100 mg |
| Test UV Absorber | 400 mg |

*potassium salt of 2-hydroxy-4,6-dichloro-s-triazine
**sodium 4,8-diisobutylnaphthalene-2-sulfonate The gelatin coats are dried at 20° C. for seven days.

When the instant UV absorbers are used, clear transparent coats are obtained which are suitable for photographic recording material for example as a UV filter coat. This is seen by measuring the % Change in Initial Optical Density (2.0) after UV exposure. The instant compounds when used in a photographic layer are extremely photostable.

EXAMPLE 33

Automotive Coating Compositions

To ascertain the effect on thermal durability and loss rate from a high solids thermoset acrylic coating containing an instant benzotriazole UV absorber, the following tests are carried out.

A high solids thermoset acrylic clear coat is prepared by mixing an experimental acrylic polyol resin and hexamethoxymethylmelamine (Resimene® 747, Monsanto) at a solids ratio of 60/40. The dodecylbenzene sulfonic acid catalyst (Nacure® 5225; King Industries) is added at 0.70% by weight. A flow aid Modaflow® (Monsanto) is added at 0.25% by weight to form a model acrylic melamine resin system.

The model clear coat is reduced with xylene to a viscosity of 26–27 second using a Zahn #2 cup and applied via a conventional air spray at 50 psi (3.5 Kg/cm$^2$) over a 1"×3" (2.54 cm×7.62 cm) quartz slide. Cure is achieved by baking the slide for 30 minutes at 260° F. (127° C.). The various test benzotriazole UV absorbers are incorporated at the 5 mmol % by weight in the clear coat. The film thickness on the quartz slides range from 1.15 to 1.41 mils (0.029 to 0.036 mm).

The films on the quartz slides are weathered according to the following conditions in Xenon Arc Weather-Ometer with a controlled irradiance at 6500 W, using inner quartz and outer borosilicate S-type filter. The irradiation cycle is as follows: 40 minutes of straight irradiation with no water spray, followed by 20 minutes of light plus front spray, followed by 60 minutes of light irradiation and finally by 60 minutes dart plus rear spray (condensation). The setting is at 0.55 W/M$^2$ at 340 nm, 1.98 kJ/hour. In the light cycle the black panel temperature is controlled at 70±2° C. The relative humidity in the light cycle is in the range of 50–55% and in the dark cycle 100%. The absorbance of the long wavelength UV band as a function of Xenon arc weathering hours are recorded.

To follow the loss of UV absorbers from the clear coats, UV spectra are measured initially and after weathering at regular time intervals. The UV spectrophotometer measures absorbance linearly up to 5.5 absorbance units using a reference beam attenuation technique.

It is assumed that the degradation products from the UV absorber do not contribute to the UV spectrum. This is tested by following the ratio of absorbance of the band at about 300 nm and the band at about 340 nm. The ratio does not change upon weathering the sample. This suggests that the UV spectrum of the weathered films correspond to the amount of UV absorber remaining in the film with very little if any contribution to the spectrum by photo degradants.

Representative benzotriazole test compounds are incorporated into a high solid thermoset acrylic melamine resin at a concentration of 3% by weight to give equal molar concentrations of the test benzotriazole in equal film thickness and sufficient to give a starting absorbance of approximately 2.0 absorbance units.

The instant benzotriazoles are especially durable in automotive coatings as judged by low loss rates.

EXAMPLE 34

Polycarbonate

Polycarbonate films of about 1 mil thickness and containing a UV absorber are prepared by dissolving polycarbonate granules (LEXAN® 145, General Electric) and UV absorbers in methylene chloride and casting the films on a glass plate using a drawdown bar. The films are exposed for 750 hours in a Xenon Arc Weather-Ometer according to ASTM G26 test method and the color change (ΔYI) versus that for unexposed films are recorded below. The color measurements (yellowness index—YI) are carried out on an ACS spectrophotometer, small area view, spectral component included d/8, D65, 10° observer, YI 1925 for unexposed and exposed samples after 750 hours.

The instant compounds are particularly efficacious when used in thermoplastic compositions, such as polycarbonate. This is shown by the reduction of yellowing (ΔYI) after exposure to actinic radiation.

EXAMPLE 35

Poly(methyl methacrylate)

The durability of representative instant benzotriazoles in thermoplastic substrates is determined by incorporating various test compounds into solvent cast films of a poly (methyl methacrylate) (PMMA) resin. The free standing films are mounted into cardboard holders, secured in metal frames and exposed in an Atlas C165 Xenon-arc Weather-Ometer under dry conditions according to ASTM G26. Loss of UV absorber is determined by monitoring the loss of diagnostic UV absorption as described earlier. Performance is measured by a change in color or the physical integrity of the film, or in loss of absorbance of the UV absorber at λmax.

Poly(methyl methacrylate), medium molecular weight, Aldrich, is dissolved in methylene chloride at room temperature along with between 1 and 3% by weight of test benzotriazole, based on the PMMA resin. Films are cast using a calibrated drawdown bar to prepare 1 mil thick film after drying.

The instant compounds are particularly efficacious when used in thermoplastic compositions, such as poly(methyl methacrylate). This is shown by the reduction in absorbance loss after exposure to actinic radiation.

EXAMPLE 36

Polycarbonate

The durability of representative instant benzotriazoles in thermoplastic substrates is determined by incorporating various test compounds into solvent cast films of polycarbonate resins. The free standing films are mounted into cardboard holders, secured in metal frames and exposed in an Atlas C165 Xenon-arc Weather-Ometer under dry conditions according to ASTM G26. Loss of UV absorber is determined by monitoring the loss of diagnostic UV absorption.

Polycarbonate flake (LEXAN® 145, General Electric) is dissolved in methylene chloride at room temperature along with between 1 and 3% by weight of test benzotriazole, based on the polycarbonate. Films are cast using a calibrated drawdown bar to prepare 1 mil thick film after drying.

The instant compounds are particularly efficacious when used in thermoplastic compositions, such as polycarbonate. This is shown by the reduction in absorbance loss after exposure to actinic radiation.

EXAMPLE 37

Pigment Stabilization in Polypropylene Fiber

The polypropylene fiber samples are prepared by extruding fiber grade polypropylene containing a pigment, a phosphite, a phenolic antioxidant or hydroxylamine, a metal stearate, a UV absorber or hindered amine light stabilizer or a combination of a UV absorber and hindered amine light stabilizer. Alternatively, the pigment is mixed with the stabilizers and then dynomilled to give a stabilized pigment composition. This stabilized pigment composition is then incorporated into polypropylene prior to spinning into fibers.

The pigment is added as a pigment concentrate which is prepared from pure pigment and polypropylene resin (PROFAX® 6301, Himont) by mixing the two components in a high shear mixer in a ratio of 25% pigment and 75% resin, pressing the resulting resin/pigment mixture on a Wabash Compression Molder (Model #30-1515-4T3) into a thin sheet and then dividing the sheed into fine chips for dispersion in fresh polypropylene resin at reduced concentrations.

All additive and pigment concentrations in the final formulations are expressed as weight percent based on the resin.

The formulations contain 0.05–0.1% phosphite, 0–1.25% phenolic antioxidant, 0–0.1% hydroxylamine, 0.05–0.1% calcium stearate, a UV absorber and/or a hindered amine stabilizer. The materials are dry-blended in a tuble dryer, extruded on a Superior/MPM 1 inch (2.54 cm) single screw extruder or a Brabender PL2000 1.25 inch (3.175 cm) single screw extruder with a general all-purpose screw (24:1 L/D) at 475° F. (246° C.), cooled in a water bath and pelletized. The resulting pellets are spun into fiber at about 525° F. (274° C.) on a HILLS Research Fiber Extruder (Model #REM-3P-24) filled with a 41 hole, delta configuration spinnerette. The spun tow is stretched at a draw ratio of 3.2:1, producing a final denier of 615/41.

The fiber samples are knitted into socks on a Lawson-Hemphill Fiber Analysis Knitter, cut into appropriate lengths and exposed in an Atlas Ci65 Xenon Arc Weather-Ometer at 89° C. black panel temperature, 0.55 W/m$^2$ at 340 nanometers and 50% relative humidity (Society of Automotive Engineers SAE J 1885 Test Procedure).

Fiber samples are tested by performing color measurements on an Applied Color Systems spectrophotometer by reflectance mode according to ASTM D 2244-79 at approximately 100 hour intervals. Identical, but separate, samples are examined for catastrophic failure approximately every 24 hours.

Phosphite is tris(2,4-di-tert-butylphenyl) phosphite.

Antioxidant is tris(3,5-di-tert-butyl-4-hydroxybenzyl) isocyanurate.

Hydroxylamine is the N,N-dialkylhydroxylamine prepared from di(hydrogenated tallow)amine by direct oxidation.

Polypropylene fibers contain the standard additives described above and is pigmented with 0.25% by weight of pigment Red BRN.

| Conc.(% by wt) UV Absorber* | Conc. (% by wt) Hindered Amine* | Delta B at 1500 hours |
|---|---|---|
| none (0%) | A (1.0%) | 37 |
| B (0.3%) | A (0.7%) | 28 |
| Compound of Example 10 (0.3%) | A (0.7%) | 24 |
| Compound of Example 10 (1.0%) | none (0%) | 14 |

*A is N,N',N'',N'''-tetrakis[(4,6-bis(butyl-(1,2,2,6,6-pentamethylpiperidin-4-yl)amino)-s-triazine-2-yl]-1,10-diamino-4,7-diazadecane, CHIMASSORB® 119, CIBA.
B is 2-(2-hydroxy-3,5-di-α-cumylphenyl)-2H-benzotriazole, TINUVIN® 234, CIBA.

The compound of instant Example 10 having both a hindered amine moiety and a benzotriazole moiety in the same molecule causes the Delta E value (measure of color change) to decrease significantly when compared to a hindered amine alone or in the physical mixture of a hindered amine and UV absorber at the same total concentration of stabilizer.

EXAMPLE 38

Pigment Stabilization in Polypropylene Fiber

The experimental and weathering procedures outlined in Example 37 are followed. Polypropylene fiber, which contains standard additives as described in Example 37, is pigmented with 0.25% by weight of pigment Yellow 183.

| Conc.(% by wt) UV Absorber* | Conc. (% by wt) Hindered Amine* | Delta E at 950 hours |
|---|---|---|
| none (0%) | A (0.6%) | 50 |
| B (0.18%) | A (0.42%) | 39 |
| Compound of Example 10 (0.6%) | none (0%) | 22 |

*A is N,N',N'',N'''-tetrakis[(4,6-bis(butyl-(1,2,2,6,6-pentamethylpiperidin-4-yl)amino)-s-triazine-2-yl]-1,10-diamino-4,7-diazadecane, CHIMASSORB® 119, CIBA.
B is 2-(2-hydroxy-3,5-di-α-cumylphenyl)-2H-benzotriazole, TINUVIN® 234, CIBA.

The compound of instant Example 10 having both a hindered amine moiety and a benzotriazole moiety in the same molecule causes the Delta E value (measure of color change) to decrease significantly when compared to a hindered amine alone or in the physical mixture of a hindered amine and UV absorber at the same total concentration of stabilizer.

EXAMPLE 39

1-Cyclohexyloxy-2,2,6,6-tetramethylpiperidin-4-yl 3-(Benzotriazol-2-yl)-5-tert-butyl-4-hydroxyhydrocinnamate This compound is prepared according to Example 2 of U.S. Pat. No. 5,021,478.

EXAMPLE 40

Pigment Stabilization in Polypropylene Fiber

The experimental and weathering procedures outlined in Example 37 are followed. Polypropylene fiber, which con tains standard additives as described in Example 37, is pigmented with 0.25% by weight of pigment Red BRN.

| Conc. (% by wt) UV Absorber* | Conc. (% by wt) Hindered Amine* | Delta E at 980 hours |
|---|---|---|
| B (0.3%) | none (0%) | 7.5** |
| none (0%) | A (0.3%) | 12.4 |
| B (0.3%) | A (0.3%) | 10.2 |
| Compound of Example 39 (0.3%) | none (0%) | 3.8 |

*A is N,N',N'',N'''-tetrakis[(4,6-bis(butyl-(1,2,2,6,6-pentamethylpiperidin-4-yl)amino)-s-triazine-2-yl]-1,10-diamino-4,7-diazadecane, CHIMASSORB® 119, CIBA.
B is 2-(2-hydroxy-3,5-di-α-cumylphenyl)-2H-benzotriazole, TINUVIN® 234, CIBA.
**This value represents the Delta E after only 326 hours. The sample becomes too brittle to read after this reading due to polymer degradation.

The compound of instant Example 39 having both a hindered amine moiety and a benzotriazole moiety in the same molecule causes the Delta E value (measure of color change) to decrease significantly when compared to a hindered amine alone. It is far superior to the physical mixture of a hindered amine and UV absorber at half the total concentration of stabilizer compared to the physical mixture of hindered amine and UV absorber.

EXAMPLE 41

Pigmented Polyamide Fiber

When the pigmented polypropylene fiber used in Example 37 is replaced with pigmented polyamide nylon 6 or 66 fiber, the instant compounds provide stabilization to the pigmented polyamide fiber far better than do conventional stabilizer systems.

EXAMPLE 42

Pigmented Polyester Fiber

When the pigmented polypropylene fiber used in Example 37 is replaced with pigmented polyester poly(ethylene terephthalate, PET) fiber, the instant compounds provide stabilization to the pigmented polyester fiber far better than do conventional stabilizer systems.

EXAMPLE 43

Dyed Polypropylene Fiber

When the pigmented polypropylene fiber used in Example 37 is replaced with dyed polypropylene fiber, the instant compounds provide stabilization to the dyed polypropylene fiber far better than do conventional stabilizer systems.

EXAMPLE 44

Dyed Polyamide Fiber

When the pigmented polypropylene fiber used in Example 37 is replaced with dyed polyamide nylon 6 or 66 fiber, the instant compounds provide stabilization to the dyed polyamide fiber far better than do conventional stabilizer systems.

EXAMPLE 45

Dyed Polyester Fiber

When the pigmented polypropylene fiber used in Example 37 is replaced with dyed polyester poly(ethylene terephthalate, PET) fiber, the instant compounds provide stabilization to the dyed polyester fiber far better than do conventional stabilizer systems.

What is claimed is:

1. A compound of formula C

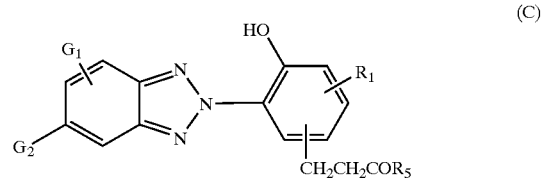

wherein
$G_1$ is hydrogen or halogen,
$G_2$ is nitro, cyano, $R_3SO$—, $R_3SO_2$—, —$COOG_3$, perfluoroalkyl of 1 to 12 carbon atoms, —$P(O)(C_6H_5)_2$, —CO-$G_3$, —CO—NH-$G_3$, —CO—N($G_3$)$_2$, —N($G_3$)-CO-$G_3$, phenyl substituted by 2,2,6,6-tetramethylpiperidin-1-yloxy,

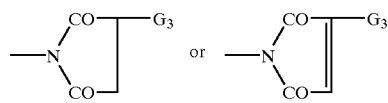

$G_3$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms;
or $G_3$ is a group formula I, II or III

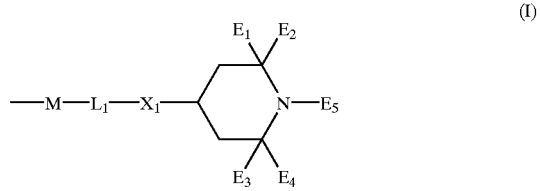

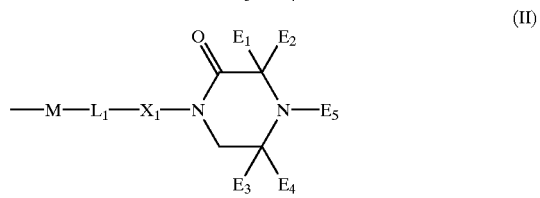

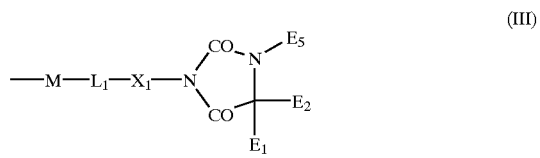

wherein
M is a direct bond, —$NG_9$-, —O—, —S—, —SO—, —$SO_2$—, —$SO_2NG_9$-, —$CONG_9$-, —COO— or —OCO—;
$L_1$ is a direct bond, alkylene of 1 to 18 carbon atoms, alkenylene of 3 to 18 carbon atoms, cycloalkylene of 5 to 12 carbon atoms, cycloalkenylene of 5 to 12 carbon atoms or said alkylene interrupted by 1 to 4 oxygen atoms;

$X_1$ is a direct bond, —COO—, —CONG$_9$-, —O— or —NG$_9$-;

$G_9$ is hydrogen or alkyl of 1 to 18 carbon atoms;

$E_1$ to $E_4$ are independently alkyl of 1 to 8 carbon atoms, or $E_1$ and $E_2$ together are pentamethylene or $E_3$ and $E_4$ together are pentamethylene;

$E_5$ is hydrogen, oxyl, straight or branched chain alkyl of 1 to 24 carbon atoms, straight or branched chain alkenyl of 3 to 24 carbon atoms, benzyl, acetyl, —CH$_2$CH(OH)-E$_8$, —OE$_9$ or —OE$_{10}$(OH)$_b$, when $E_5$ is —OE$_{10}$(OH)$_b$, $G_2$ may also be hydrogen or halogen;

$E_8$ is hydrogen, methyl, ethyl or phenyl, $E_9$ is hydrogen, straight or branched chain alkyl of 1 to 24 carbon atoms, cycloalkyl of 5 to 12 carbon atoms, straight or branched chain alkenyl of 3 to 24 carbon atoms, cycloalkenyl of 5 to 12 carbon atoms, phenylalkyl of 7 to 15 carbon atoms, a radical of a saturated or unsaturated bicyclic or tricyclic hydrocarbon of 7 to 15 carbon atoms, aryl of 6 to 10 carbon atoms or said aryl substituted by one to three alkyl of 1 to 4 carbon atoms; or a group of formula IV

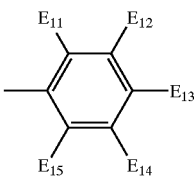

(IV)

$E_{10}$ is a straight or branched chain alkyl of 1 to 24 carbon atoms, cycloalkyl of 5 to 12 carbon atoms, cycloalkenyl of 5 to 12 carbon atoms, straight or branched chain alkenyl of 3 to 24 carbon atoms, phenylalkyl of 7 to 15 carbon atoms, phenyl or said phenyl substituted by one to three alkyl of 1 to 4 carbon atoms;

b is 1, 2 or 3 with the restriction that b cannot exceed the number of carbon atoms in $E_{10}$, and if b is 2 or 3, each hydroxyl group is attached to a different carbon atom of $E_{10}$;

$E_{11}$ to $E_{15}$ are independently hydrogen, halogen, nitro, cyano, alkyl of 1 to 18 carbon atoms, phenylalkyl of 7 to 15 carbon atoms, aryl of 6 to 10 carbon atoms, hydroxyl, carboxyl, alkylthio of 1 to 18 carbon atoms, alkoxy or 1 to 18 carbon atoms, phenylalkoxy of 7 to 15 carbon atoms, aryloxy of 6 to 10 carbon atoms, alkylcarbonyloxy of 2 to 18 carbon atoms, alkylsulfonyl of 1 to 18 carbon atoms, arylsulfonyl of 6 to 15 carbon atoms, sulfo or phosphono, or any two vicinal substituents connected together to form a mono- or polycyclic ring;

$R_1$ is hydrogen, straight or branched chain alkyl of 1 to 24 carbon atoms, straight of branched chain alkenyl of 2 to 18 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_1$ is a group I, II, III, V or VI

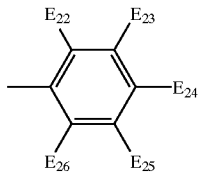

(V)

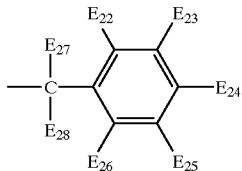

(VI)

where $E_{27}$ and $E_{28}$ are independently alkyl of 1 to 18 carbon atoms, or cycloalkyl of 5 to 12 carbon atoms;

$E_{22}$, $E_{23}$, $E_{24}$, $E_{25}$ and $E_{26}$ are independently hydrogen, halogen, straight or branched alkyl of 1 to 18 carbon atoms, alkenyl of 2 to 18 carbon atoms, said alkyl or said alkenyl substituted by one or more halogen, —OCOR$_{11}$, —OR$_4$, —NCO, —NHCOR$_{11}$ or —NR$_7$R$_8$, or mixtures thereof, where $R_4$ is straight or branched chain alkyl of 1 to 24 carbon atoms or straight or branched chain alkenyl of 2 to 18 carbon atoms; or said alkyl or said alkenyl interrupted by one or more —O—, —NH— or —NR$_4$— groups or mixtures thereof and which can be unsubstituted or substituted by one or more —OH, —OR$_4$ or —NH$_2$, or mixtures thereof; or $E_{22}$, $E_{23}$, $E_{24}$, $E_{25}$ and $E_{26}$ are independently phenyl, —OH, —OCOR$_{11}$, —OE$_{29}$, —NCO, —NHCOR$_{11}$ or —NR$_7$R$_8$, cyano, nitro, perfluoroalkyl of 1 to 12 carbon atoms, —COG$_3$, —COOG$_3$, —CON(G$_3$)$_2$, —CONHG$_3$, R$_3$S—, R$_3$SO—, R$_3$SO$_2$—, —P(O)(C$_6$H$_5$)$_2$, —P(O)(OG$_3$)$_2$ or —SO$_2$—X$_2$-E$_{29}$;

$X_2$ is —O—, —NH— or —NR$_4$—;

$E_{29}$ is straight or branched chain alkyl of 1 to 24 carbon atoms, straight or branched chain alkenyl of 2 to 18 carbon atoms, said alkyl or said alkenyl substituted by one or more —OH, —OCOR$_{11}$, —OR$_4$, —NCO, —NHCOR$_{11}$, —NR$_7$R$_8$, phthalimido,

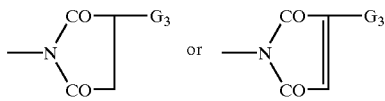

or mixtures thereof, where $R_4$ is straight or branched chain alkyl of 1 to 24 carbon atoms or alkenyl of 2 to 18 carbon atoms; or said alkyl or said alkenyl interrupted by one or more —O—, —NH— or —NR$_4$— groups or mixtures thereof and which can be unsubstituted or substituted by one or more —OH, —OR$_4$ or —NH$_2$, or mixtures thereof; or $E_{29}$ is phenyl or phenylalkyl of 7 to 15 carbon atoms, or said phenyl or said phenylalkyl substituted by one to three alkyl groups of 1 to 4 carbon atoms;

$R_5$ is a group of formula I;

$R_7$ and $R_8$ are independently hydrogen, alkyl of 1 to 18 carbon atoms, straight or branched chain $C_3$–$C_{18}$alkyl which is interrupted by —O—, —S— or —NR$_{11}$—, $C_5$–$C_{12}$cycloalkyl, $C_6$–$C_{14}$aryl or $C_1$–$C_3$hydroxyalkyl, or $R_7$ and $R_8$ together with the N atom are a pyrrolidine, piperidine, piperazine or morpholine ring, $R_{11}$ is hydrogen, straight or branched chain $C_1$–$C_{18}$alkyl, $C_5$–$C_{12}$cycloalkyl, straight or branched chain $C_3$–$C_8$alkenyl, $C_6$–$C_{14}$aryl or $C_7$–$C_{15}$aralkyl, $R_3$ is alkyl of 1 to 20 carbon atoms, hydroxyalkyl of 2 to 20 carbon atoms, alkenyl of 3 to 18 carbon atoms, cycloalkyl of 5 to 12 carbon atoms, phenylalkyl of 7 to 15 carbon atoms, aryl of 6 to 10 carbon atoms or said aryl substituted by one or two alkyl of 1 to 4 carbon atoms or 1,1,2,2-tetrahydroperfluoroalkyl where the perfluoroalkyl moiety is of 6 to 16 carbon atoms, and with the proviso that (c) when $G_2$ is —$COOG_3$ and $G_3$ is of group I, then $E_5$ of group I is not hydrogen, oxyl, $C_1$–$C_{12}$alkyl, $C_3$–$C_8$alkenyl, benzyl, acetyl, or a group —$CH_2$—CH(OH)-$E_8$.

2. A compound selected from the group consisting of (a) 1-(2-hydroxy-2-methylpropoxy-2,2,6,6-tetramethylpiperidin-4-yl 3-(5-chlorobenzotriazol-2-yl)-5-tert-butyl-4-hydroxyhydrocinnamate;

(k) 2,2,6,6-tetramethylpiperidin-4-yl 3-(5-phenylsulfonylbenzotriazol-2-yl)-5-tert-butyl-4-hydroxyhydrocinnamate;

(l) 1,2,2,6,6-pentamethylpiperidin-4-yl 3-(5-phenylsulfonylbenzotriazol-2-yl)-5-tert-butyl-4-hydroxyhydrocinnamate;

(m) 1-(2,4-dibromophenoxy)-2,2,6,6-tetramethylpiperidin-4-yl 3-(5-chlorobenzotriazol-2-yl)-5-tert-butyl-4-hydroxyhydrocinnamate; and (n) 1-(2-nitro-4-chlorophenoxy)-2,2,6,6-tetramethylpiperidin-4-yl 3-(5-chlorobenzotriazol-2-yl)-5-tert-butyl-4-hydroxyhydrocinnamate.

* * * * *